US012751698B2

(12) United States Patent
Johnson et al.

(10) Patent No.: US 12,751,698 B2
(45) Date of Patent: Oct. 6, 2026

(54) SAMPLE COLLECTION DEVICE, SAMPLE COLLECTION KIT, SAMPLE COLLECTION SYSTEM, DIAGNOSTIC DEVICE, AND ASSOCIATED METHODS

(71) Applicant: ASAP BreatheAssist Pty Ltd, Cremorne (AU)

(72) Inventors: Michael Ralph Burgess Johnson, Hawthorn (AU); Justin Robert Armistead, The Basin (AU); Toby James Hartley, Ferntree Gulley (AU)

(73) Assignee: ASAP BreatheAssist Pty Ltd, Cremorne (AU)

( * ) Notice: Subject to any disclaimer, the term of this patent is extended or adjusted under 35 U.S.C. 154(b) by 596 days.

(21) Appl. No.: 18/015,953

(22) PCT Filed: Jul. 13, 2021

(86) PCT No.: PCT/AU2021/050745
§ 371 (c)(1),
(2) Date: Jan. 12, 2023

(87) PCT Pub. No.: WO2022/020877
PCT Pub. Date: Feb. 3, 2022

(65) Prior Publication Data

US 2024/0032898 A1 Feb. 1, 2024

(30) Foreign Application Priority Data

Jul. 13, 2020 (AU) ................................ 2020902417
Sep. 29, 2020 (AU) ................................ 2020903519
(Continued)

(51) Int. Cl.
*A61B 10/00* (2006.01)
*A61M 15/08* (2006.01)
(Continued)

(52) U.S. Cl.
CPC ....... *A61B 10/0045* (2013.01); *A61M 15/085* (2014.02); *A61M 21/02* (2013.01);
(Continued)

(58) Field of Classification Search
None
See application file for complete search history.

(56) References Cited

U.S. PATENT DOCUMENTS 1,077,574 A 11/1913 Woodward
1,481,581 A 1/1924 Woodward
(Continued)

FOREIGN PATENT DOCUMENTS

AU 2013204827 A1 2/2014
AU 2013205674 A1 2/2014
(Continued)

OTHER PUBLICATIONS

International Search Report and Written Opinion mailed Sep. 21, 2021 for International Application No. PCT/AU2021/050745.
(Continued)

*Primary Examiner* — Alex M Valvis
(74) *Attorney, Agent, or Firm* — Wolf, Greenfield & Sacks, P.C.

(57) ABSTRACT

The invention provides a sample collection device (1) for collection of a nasal sample from an individual. The sample collection device comprises: a frame (2) having at least one frame member (4) configured to be received and retained or accommodated within a nostril of the individual; and a collector element (8) provided on and/or carried by the at least one frame member (4) for receiving and collecting the nasal sample, which sample is usually in a liquid or semi-solid form. The collector element (8) is provided on and/or carried by the frame member (4) such that, when the frame member (4) is retained or accommodated within a nostril,
(Continued)

the collector element (8) contacts and/or engages with an inner surface or tissue of the nasal cavity to receive and collect the sample. The invention also provides a sample collection kit (20) comprising the sample collection device (1) and a sample container (21) for receiving and storing the collector element (8). The invention further provides a diagnostic kit and a diagnostic device comprising a sample collection device (1) as well as associated methods.

28 Claims, 12 Drawing Sheets

(30) Foreign Application Priority Data

Oct. 16, 2020 (AU) ................................ 2020903763
Nov. 19, 2020 (AU) ................................ 2020904284

(51) Int. Cl.
*A61M 21/00* (2006.01)
*A61M 21/02* (2006.01)
*A61M 31/00* (2006.01)
*A61M 37/00* (2006.01)

(52) U.S. Cl.
CPC ........ *A61M 31/00* (2013.01); *A61M 37/0015* (2013.01); *A61M 2021/0077* (2013.01); *A61M 2037/0023* (2013.01); *A61M 2210/0618* (2013.01)

(56) References Cited

U.S. PATENT DOCUMENTS

| | | | | |
|---|---|---|---|---|
| 4,887,597 | A | 12/1989 | Holland | |
| RE35,408 | E | 12/1996 | Petruson | |
| 5,931,852 | A | 8/1999 | Brennan | |
| 8,834,512 | B1 | 9/2014 | Brown et al. | |
| D952,141 | S | 5/2022 | Pepper et al. | |
| 2003/0106555 | A1* | 6/2003 | Tovey | A61F 5/08 128/205.27 |
| 2004/0161804 | A1* | 8/2004 | McCash | G01N 33/5695 435/7.2 |
| 2006/0018800 | A1 | 1/2006 | Slowey et al. | |
| 2006/0185677 | A1 | 8/2006 | Brown | |
| 2006/0207598 | A1 | 9/2006 | Thomas | |
| 2007/0088334 | A1 | 4/2007 | Hillis et al. | |
| 2007/0184495 | A1* | 8/2007 | Shaari | G01N 33/53 435/7.9 |
| 2010/0042134 | A1 | 2/2010 | Wien | |
| 2010/0312133 | A1* | 12/2010 | Bazemore | A61B 5/097 128/205.27 |
| 2011/0118775 | A1 | 5/2011 | Brown | |
| 2011/0152875 | A1* | 6/2011 | Gonzales | A61M 27/002 606/108 |
| 2012/0116325 | A1 | 5/2012 | Hunt et al. | |
| 2012/0330345 | A1 | 12/2012 | Tasca | |
| 2014/0128904 | A1 | 5/2014 | Mezzoli et al. | |
| 2014/0246023 | A1 | 9/2014 | Maryanka | |
| 2014/0296667 | A9 | 10/2014 | Dahl et al. | |
| 2015/0000675 | A1 | 1/2015 | Kallikounis et al. | |
| 2015/0196420 | A1 | 7/2015 | Ede et al. | |
| 2016/0367773 | A1 | 12/2016 | Davi | |
| 2017/0172783 | A1 | 6/2017 | Pepper et al. | |
| 2017/0273626 | A1* | 9/2017 | MacDonald | A61B 5/087 |
| 2018/0168846 | A1 | 6/2018 | Johnson et al. | |
| 2021/0321991 | A1* | 10/2021 | Elliott | A61B 10/02 |
| 2022/0080138 | A1 | 3/2022 | Pepper et al. | |
| 2024/0416055 | A1 | 12/2024 | Johnson et al. | |

FOREIGN PATENT DOCUMENTS

| | | | | |
|---|---|---|---|---|
| CN | 109045447 A | | 12/2018 | |
| CN | 109663205 A | | 4/2019 | |
| JP | 2013-518259 A | | 5/2013 | |
| JP | 2015-121462 A | | 7/2015 | |
| JP | 2019-171011 A | | 10/2019 | |
| WO | WO 2004/026391 A1 | | 4/2004 | |
| WO | WO 2012/137182 A2 | | 10/2012 | |
| WO | WO 2015/192162 A1 | | 12/2015 | |
| WO | WO 2015/192173 A1 | | 12/2015 | |
| WO | WO-2018183421 A1 | * | 10/2018 | A61B 10/0045 |
| WO | WO 2020/150787 A1 | | 7/2020 | |

OTHER PUBLICATIONS

International Preliminary Report on Patentability mailed Oct. 28, 2022 for International Application No. PCT/AU2021/050745.

International Search Report and Written Opinion mailed Aug. 30, 2021 for International Application No. PCT/AU2021/050746.

International Preliminary Report on Patentability mailed Oct. 27, 2022 for International Application No. PCT/AU2021/050746.

Extended European Search Report mailed Aug. 7, 2024 for EP Application No. EP21850592.3.

* cited by examiner

SAMPLE COLLECTION DEVICE, SAMPLE COLLECTION KIT, SAMPLE COLLECTION SYSTEM, DIAGNOSTIC DEVICE, AND ASSOCIATED METHODS

CROSS-REFERENCE TO RELATED APPLICATIONS

This application is a national stage filing under 35 U.S.C. § 371 of International Patent Application No. PCT/AU2021/050745, filed Jul. 13, 2021, which claims priority to Australian Application No. 2020904284, filed Nov. 19, 2020, Australian Application No. 2020903763, filed Oct. 16, 2020, Australian Application No. 2020903519, filed Sep. 29, 2020, and Australian Application No. 2020902417, filed Jul. 13, 2020. The entire contents of these applications are incorporated herein by reference in their entirety.

TECHNICAL FIELD

The present disclosure relates to a sample collection device, and especially to a device for collecting a nasal sample, as well as a sample collection kit, a sample collection system, and a method of collecting a nasal sample. The present disclosure also relates to a diagnostic kit or a diagnostic device including a test or assay for testing the sample on or in association with the sample collection device, and an associated method.

The present disclosure has particular application to collection of a microbiological specimen in a sample of mucus collected from the nostril(s) of an individual, and it will be convenient to describe the subject of the present disclosure in this exemplary context. It will be appreciated, however, that the disclosure is not limited to this particular application but may be used for collecting a sample for a range of different tests and purposes.

BACKGROUND ART

The following discussion of background art in this specification should in no way be considered an admission that such background is prior art, nor that such background is widely known or forms part of the common general knowledge in the field in Australia or in any other country worldwide.

In order to test individuals for the presence of infection or disease, it is common practice to take a biological sample from the individual, e.g. of mucus, blood, urine, etc., and to test the sample for the presence of one or more pathogens or for the presence of one or more substances that may indicate a particular condition. Sample collection need not be restricted individuals suffering acute symptoms. Rather, sample collection can also be conducted to screen a whole population or parts thereof for the presence of a pathogen e.g. a respiratory virus. When testing for respiratory illnesses, samples or specimens may be obtained using nasal and throat swabs, typically by a healthcare professional at the point of care. The collection of specimens from the surface of the respiratory mucosa with nasopharyngeal swabs is a procedure used, for example, in the diagnosis of Covid-19 in adults and children, the illness caused by infection with the severe acute respiratory syndrome coronavirus 2 (SARS-CoV-2). But the procedure can also be used to evaluate patients with suspected respiratory infection caused by other viruses (e.g., influenza virus, rhinovirus) and some bacteria (e.g., *Staphylococcus, Streptococcus*). Samples are then usually sent to laboratories for analysis.

The significant amount of testing carried out during the Covid-19 pandemic has drawn attention to a number of issues with the conventional use of nasopharyngeal swabs in the collection of biological samples for testing. Firstly, the sample collection procedure is quite invasive and is likely to cause discomfort for the individual from whom the sample is collected. In this regard, nasopharyngeal swabs have a long shaft made of plastic or metal with a tip made of polyester, rayon, or flocked nylon and these swabs are inserted through the nasal passage deep into the nasopharynx. Secondly, to be performed well and reliably, the sample collection procedure requires a high degree of care and skill by the medical practitioner taking the sample. If a sample is not collected well or in the correct manner, the sample may provide an inadequate specimen for a conclusively positive test result despite the individual being infected with a disease, such as Covid-19, thus giving rise to a misdiagnosis or a so-called "false negative". Thirdly, the need for individuals to attend a clinic to be tested exposes the medical staff working at the point of care in the clinics and/or conducting the tests to a higher risk of contracting the disease themselves, not to mention the fact that potentially infected individuals are thereby also required to travel through their community, possibly on public transport, in order to attend the clinic to be tested, thereby also increasing the risk of the disease being transmitted within the community. The conventional testing regimes that rely on conventional nasopharyngeal swabs therefore present a number of problems.

In view of the above, it would be desirable to provide a new sample collection device, especially for collecting a nasal sample. Further, it would be desirable to provide such a device that substantially overcomes or at least ameliorates one or more of the above problems. It would also be desirable to provide a new sample collection kit, and a new sample collection system and method for collecting a nasal sample. It would further be desirable to provide a new diagnostic device or diagnostic kit which includes a sample collection device, and a related method.

SUMMARY OF THE DISCLOSURE

According to one aspect, the disclosure provides a sample collection device for collection of a nasal sample from an individual. The sample collection device comprises: a frame having at least one frame member configured to be received and retained or accommodated within a nostril of the individual; and a collector, e.g., a collector element, provided on and/or carried by the at least one frame member for receiving and collecting the nasal sample, which is preferably in the form of a liquid or semi-solid. The collector element is provided on and/or carried by the frame member such that, when the frame member is retained or accommodated within a nostril, the collector element contacts or engages with an inner surface (e.g., tissue) of the nostril to receive and collect the sample.

In this way, the present disclosure provides an alternative to a conventional nasopharyngeal swab. The sample collection device of the disclosure has a collector, such as a collector element, which itself is preferably be in the form of a swab, provided on and/or carried by a frame member that is received and retained or accommodated within a nostril of the individual to collect the sample there. In other words, a highly invasive introduction of a swab to the nasopharynx is not required and, as a consequence, an individual to be tested is able to insert the sample collection device him-/herself. Also, because use of the sample collection device of the disclosure does not require assistance by another person, let alone a skilled medical practitioner, it is highly suited to use outside of a clinical practice or a clinical environment, such as, for example, at home.

It will be noted that the reference to a "sample" is understood to include any liquid, semi-solid, solid, or air-borne matter that may be collected from an individual, particularly from the nose (e.g., a nasal cavity) of the individual. Thus, the sample collected from an individual will typically comprise mucus and/or other nasal secretion produced by and/or able to be collected from the nose. The sample may form or provide a specimen for testing for the presence of any one or more of a pathogen (e.g. a bacteria, virus, fungus, or a cellular component thereof, like genomic DNA and/or RNA, mitochondrial DNA, proteins, carbohydrates and/or lipids), an antibody, a neoplastic cell, molecule or other substance or compound that may provide an indication of a particular disease or condition of the individual. For example, the testing could be for the presence of a metal, metal oxide, or trace element produced during respiration.

In a preferred embodiment, the sample collection device is wearable; that is, the device is configured to be worn by the individual such that the collector element, which is provided on and/or carried by the at least one frame member, is received and retained or accommodated within the nostril of the individual for an extended and/or predetermined period of time for sample collection. In this regard, the sample collection time is preferably in the range of about 5 minutes to about 8 hours, more preferably in the range of about 10 minutes to about 4 hours. Depending on the condition of the individual from whom the sample is being collected (e.g., how 'productive' the nasal cavity is). However, the sample collection time could be lower, but will typically be at least about 15 seconds, preferably at least about 30 seconds, and more preferably at least about one or two minutes. This sample collection time is to be contrasted with conventional use of nasopharyngeal swabs in which the sample is collected within a matter of only a few seconds. The significantly longer sample collection time which arises or is achieved by the 'wearability' of the device increases a likelihood of a high 'sample load' on the collector element of the device, and may thereby increase the prospects of obtaining a sample that will provide an accurate representation of the individual's condition during testing.

In a particular preferred embodiment, the sample collection device may include a timing indicator or means for indicating to the individual or wearer when a predetermined sample collection time has elapsed. In this regard, the indicator may be provided on a part of the frame that is external of the nostril(s), and therefore visible (e.g., in a mirror for the wearer), during use of the device. In a particular preferred embodiment, the timing indicator may comprise a patch that is configured to change appearance (e.g. to change colour) over time. For example, the indicator patch could include a substance selected to react with air and/or with light over the predetermined time period in order to change its colour over that time. Upon commencing use of the device, therefore, the indicator patch may be initially exposed to air and/or to light (e.g., by removing a protective covering, that could be provided as removable adhesive cover or label). After the predetermined sample collection time has elapsed, the indicator patch will have changed colour due to exposure to air and/or light to indicate to the user or wearer that the sample collection device can now be removed. In this way, the device can be designed to achieve consistency of use by individuals testing themselves.

In a preferred embodiment, the at least one frame member on which the collector, e.g., collector element, is provided or carried is configured to be received and retained or accommodated within the anterior nasal cavity, e.g., within the nares or nasal vestibule, for receiving and collecting the nasal sample. In this regard, scientific literature indicates that the nares are valid for the collection of nasal mucus for a nasal swab specimen, including for the Covid-19 disease. This region of the nose is also directly accessible by the individual him-/herself and simplifies the introduction and positioning of the sample collection device within the nostril(s).

In a preferred embodiment, the at least one frame member on which the collector, e.g., collector element, is provided and/or carried is preferably elongate and preferably extends as a rib which may follow a profile or curvature of an inner surface of the nostril. In this regard, the frame member or rib member may be formed to complement a surface profile or curvature of the nasal cavity, which naturally enhances comfort for the wearer and also serves to improve contact between the collector element and the inner surface or tissue of the nasal cavity. To this end, the frame member or rib member of the sample collection device on which the collector element is provided or carried preferably has a curved or looped configuration. In this regard, the elongate frame member (or rib member) may exhibit an arcuate or arched profile which approximates at least a portion of a circle, an ellipse or a parabola. This enables the frame member to be received and to seat within the nostril comfortably and consistently, which is important for achieving both consistency in use and consistency in sample collection. The collector element is typically provided and/or carried on a surface or region of the frame member that faces the tissue of the nasal cavity. In the context of wearer comfort and ease of introduction into the nostril, the elongate frame member is preferably relatively soft, resiliently flexible and is preferably configured to be biased into contact with the nostril so that the collector element engages with tissue of the nasal cavity when accommodated therein.

In a preferred embodiment, the at least one frame member on which the collector element is provided or carried is configured to be broader or wider in a region thereof to be located deeper within the nasal cavity or nares. In this way, the frame member provides a larger surface area for bringing the collector element provided or carried thereon into contact with nasal tissue in an area of the nasal cavity or nares likely to provide a greater sample load to be collected. For similar reasons, the at least one frame member may be divided, splayed or open in this region to provide a greater surface area for supporting the collector (which collector/collector element may include fibres, e.g., flocked fibres), thereby to increase a potential sample load.

In a preferred embodiment, the frame comprises a pair of frame members, each of which is configured to be accommodated within a respective one of the nostrils of the individual. Thus, the device preferably comprises a respective collector/collector element provided on and/or carried by each of those frame members such that each collector or collector element contacts, bears against and/or engages with the inner wall or tissue of a respective one of the nostrils to receive and collect the sample. As will be appreciated, the collection device is therefore preferably configured with frame members and collector elements designed to be received and retained in both of the nostrils of the individual simultaneously. In view of the naturally occurring physiological congestion of the nasal conchae (nasal cycle), which causes alternating partial congestion and decongestion of the nasal cavities in humans naturally, it is beneficial if the sample is collected from both nasal cavities simultaneously. It is also preferable that, when deployed or accommodated within the nostrils, the sample collection device will not fully obscure or block the nasal passages but will still allow the individual to breathe through the nose. Nevertheless, it may possibly be more comfortable for the individual to breathe through the mouth during use of the sample collection device.

In a preferred embodiment, the or each collector element of the sample collection device is designed or adapted to be separated or removed from the frame to harvest the sample collected thereon for testing. This has practical advantages from a point of view of handling and transport of the sample, and it is envisaged that this may be achieved in a variety of ways. For example, in a particular preferred embodiment, the or each collector element may be configured in the form of a sleeve of collector material designed to extend over an outer periphery of the respective frame member on which it is provided and/or carried. The sleeve of collector material may thus be removable from the frame member (e.g., to be pulled off or drawn off the frame member) for harvesting the sample collected thereon for testing. In another particular preferred embodiment, the or each collector element may be connected or fixed (e.g., fused or bonded) to a respective frame member on which it is provided or carried at one or more connection points, and the one or more connection points may be releasable (e.g., frangible or configured to break) to permit the separation or removal of the collector element from the frame upon the application of a suitable force. In yet a further particular preferred embodiment, the or each frame member includes a separation point at which that frame member carrying the collector element is adapted to be physically separated from the frame to harvest the sample collected on the collector element for testing. The separation point may comprise a point of weakness (e.g., a fracture point) at which the or each frame member is configured to be separated or broken away from the frame upon application of a suitable force. In this regard, the point of weakness or the separation point may comprises a region of reduced thickness, such as a necked or notched region of the frame member. A notch may facilitate fracture by providing for stress concentration.

In a preferred embodiment, the or each collector element of the sample collection device may be integrated or integrally formed with the frame member upon which it is provided or carried. In this regard, the collector element may be comprised of the same material as the frame member and may, for example, form an outer region or layer of the frame member for receiving the nasal sample. Thus, in certain embodiments, the material of the frame member may potentially perform a dual role as a collector element also.

In a preferred embodiment, the frame of the sample collection device includes a handle portion for manual handling of the device by the individual. In this regard, the or each frame member on which the collector element(s) is/are provided or carried desirably extend/s from the handle portion. The handle portion thus enables a user to manipulate the sample collection device by hand without handling and potentially contaminating the collector elements; e.g. both before and after collection of the sample. The handle portion is preferably arranged centrally of the device and may be located between the two frame members configured to be received and accommodated within the respective nostrils. In order to provide greater clarity for the individual user which part(s) of the sample collection device should and should not be touched by hand, the device may be colour coded. That is, the handle portion may be clearly marked or coloured to identify that manual handling is permitted, and other parts of the device may be differently marked or coloured to reflect that manual handling of those parts is to be avoided. The timing indicator described above for providing an indication of the sample collection time may preferably be provided on the handle portion. The handle portion is optionally removably connected to the frame or to the or each said frame member on which a respective collector is provided or carried.

In a particular preferred embodiment, the frame of the sample collection device includes a part which is configured or designed to remain largely outside of or external to the nostrils in use. This part of the frame thus preferably incorporates the handle portion described above. This 'external' part of the frame may interconnect the frame members on which the respective collector elements are provided or supported. To this end, this 'external' part of the frame may include a generally U-shaped body comprising a pair of leg members, each of which connects to the respective frame members with the collector elements. In use, therefore, the U-shaped body is arranged to span a septum of a nose when worn by an individual, with the leg members extending into each nostril on either side of the septum. The distal end regions of the leg members may be arranged, in use, to engage with the septum and extend from the septum behind the columella and alar fibrofatty tissue of the nose, allowing the frame members on which the collector elements are carried, in use, to extend along respective nasal orifices to an inner wall of the nostrils.

In a preferred embodiment, the frame includes a sample collection accelerator to promote excretion of nasal mucus. In this regard, the accelerator preferably comprises a source of a substance for inhalation by the individual to promote the excretion of nasal mucus. The source is preferably supported on the frame, e.g., as a pad impregnated with the substance to be inhaled, and is configured to be positioned adjacent the individual's nostrils when each frame member on which a respective collector element is provided or carried is received and accommodated within a nostril. The sample collection accelerator is preferably provided on the external part of the fame, e.g., the handle portion or the U-shaped body of the frame, and thus may operate to reduce the predetermined time period for sample collection.

In a preferred embodiment, each collector element comprises a collector material for receiving and collecting the nasal sample. As noted above, each collector element is preferably in the form of a swab. Accordingly, the collector material may be comprised of fibres, such as flocked fibres, compressed fibres, fibre sheet, knitted fibres, and/or of a foam for absorbing and retaining the sample. In the case of the collector material being comprised of fibres, the collector material may, for example, be selected from a group consisting of cotton, rayon, calcium alginate, polyester, polypropylene, polyamide (e.g., Nylon), and polyethylene. In the case of the collector material being comprised of a foam material, the material may, for example, comprise a urethane foam. As noted above, in a preferred embodiment each collector element may be in the form of a sleeve of collector material, e.g., a sleeve of knitted fibres, a flocked sleeve, an extruded sleeve, or a foam sleeve. In an alternative preferred embodiment, the collector element may be in the form of a pad of collector material, such as a pad of compressed fibres, an extruded pad of fibres, a pad of knitted fibres, or pad of foam material. As also noted above, the collector element may optionally be integrated or integrally formed with the frame member upon which it is provided or carried. Where, for example, the collector element comprises a foam material, it could be provided or formed as an outer region or layer of a frame member comprised of the same foam material.

In a preferred embodiment, the frame, or each said at least one frame member, forms a substrate of the device and is comprised of a polymer plastic material, which is preferably selected from the group consisting of polypropylene (PP), polyamide (PA) e.g., Nylon, polyethylene (PE), polystyrene (PS), and/or styrene-ethylene-butylene-styrene (SEBS). Alternatively, or in addition, the substrate of the device (i.e., the frame and/or each said at least one frame member) may be comprised of metal wire.

According to a further aspect, the present disclosure provides a frame of a sample collection device for collecting a nasal sample from an individual. The frame of the sample collection device comprises at least one frame member configured to be received and retained or accommodated within a nostril of the individual. The at least one frame member is configured or adapted to carry or support a collector element for receiving and collecting the nasal sample, such that, when the frame member is accommodated and/or retained within a nostril, the collector element contacts and/or engages with an inner surface or tissue of the nasal cavity to receive and collect the sample.

As noted above, in a preferred embodiment, the at least one frame member is formed to complement a surface profile or curvature of the nasal cavity, and the at least one frame member is configured or adapted to carry or support the collector element on a surface or region of the frame member that faces the tissue of the nasal cavity. The at least one frame member is resiliently flexible and biased into contact with the nasal cavity so that the collector element bears against and/or engages with tissue of the nasal cavity when the frame member is accommodated within a nostril.

In a preferred embodiment, the frame includes a pair of the frame members, each of which is configured to be accommodated within a respective one of the nostrils of the individual. Each of the frame members is configured or adapted to carry or support a respective collector element such that each collector element bears against or engages with the tissue of the respective nostril to receive and collect the sample. As discussed above, the frame may include a handle portion for manual handling by the individual. The/each frame member may extend from the handle portion of the frame and preferably has a curved or looped configuration. The/each frame member may have a separation point, such as a point of weakness or fracture point, at which the frame member is designed to be separated from the frame to harvest the collector element for testing the sample.

According to another aspect, the present disclosure provides a sample collection device for collection of a nasal sample from an individual, the sample collection device comprising: a substrate configured to be received and retained or accommodated within a nostril of the individual; and a collector (e.g., collector element) provided on or carried by the substrate for receiving and collecting the nasal sample, preferably in the form of a liquid or semi-solid. The collector or collector element is provided on or carried by the substrate such that, when the substrate is retained or accommodated within a nostril, the collector/collector element contacts or engages with an inner wall or surface (e.g., tissue) of the nostril to receive and collect the sample.

In a preferred embodiment, the substrate forms a frame of the sample collection device for supporting the collector element provided or carried thereon. Preferably, the frame comprises at least one frame member configured to be received and retained or accommodated within the nostril of the individual, and the collector element is provided on and/or carried by the frame member. As noted above, the substrate is configured to be received and retained or accommodated within the anterior nasal cavity, e.g., within the nares or the nasal vestibule, for receiving and collecting the nasal sample. In this way, the sample collection device is preferably configured to be worn by the individual.

In a preferred embodiment, the substrate or frame of the sample collection device comprises a framework structure, such as an open framework structure, preferably in the form of or comprising an array, web, or mesh of strand-like elements or filaments. The elements, strands, or filaments of this framework structure, array, web, or mesh preferably comprise or are formed of a polymer plastic material and may be fused or bonded together to form the substrate/frame of the sample collection device. In this regard, the framework structure is preferably formed in an additive manufacturing or '3D printing' process. The framework structure is desirably relatively soft and flexible in the hand of a user.

In a preferred embodiment, the collector or the collector element provided on or carried by the substrate/frame of the sample collection device for receiving and collecting the nasal sample comprises an open framework, preferably formed as an array, web, or mesh of strand-like elements or filaments, which may comprise an outer layer or covering on the substrate or frame of the device. The elements, strands, and/or filaments of the open framework comprising the collector or the collector element are typically formed of a polymer plastic material and may be fused or bonded together. In this regard, the open framework or the array, web, or mesh comprising the collector or the collector element may be formed in an additive manufacturing or 3D printing process. The open framework or the array, web or mesh of strands or filaments in the collector or collector element is desirably very soft and flexible in the hand of an individual user and very soft to the touch upon insertion into the nasal cavity. This promotes user comfort and avoids any risk of tissue damage during the use. The open framework structure of each collector or collector element creates pores or apertures or voids for receiving and retaining the mucus of the nasal sample which have a size larger than is typically provided by fibre flocking or foam material. In this way, such an open filament framework can promote better ingress or uptake of the nasal sample by the collector element during sample collection and also promote better release or elution of the sample during harvesting.

In a preferred embodiment, the sample collection device is provided with a unique identifier for use in recording or registering an individual from whom a sample is collected with the device associated with the collected sample. In this way, the unique identifier is designed to support data integrity and sample tracking. The unique identifier may be in the form of a number, a symbol, a code, a signal, or any other form suitable for creating a unique identity for the device. The unique identifier may be physically provided in or on the device itself, e.g. in or on the substrate or frame of the device, or in association with the device; e.g. in or on packaging.

In a preferred embodiment, the unique identifier is adapted to be recognised or recorded automatically when registering the individual from whom a sample is collected with the device. In one particular preferred embodiment, the unique identifier is provided in the form of a code (e.g. a QR code) which is able to be scanned or read in an automated way e.g., via QR code-recognition software in a mobile phone application. That code may be provided on the device itself or on the packaging associated with the device. In another particular preferred embodiment, the unique identifier is provided in the form of a signal, e.g., a radio-frequency signal via an RFID device, which is able to be scanned or read in an automated manner. A signal emitter (e.g., RFID) for emitting the unique identifier signal may again optionally be provided in or on the device itself. Once the unique identifier has been scanned or read to record the specific sample collection device, personal details of the individual from whom the sample is collected with that device may then be registered (e.g., name, address, gender, date of birth, health insurance details, etc.) to a database.

According to a further aspect, the present disclosure provides a sample collection kit, comprising a sample collection device according to any of the embodiments described above for collecting a nasal sample; and a sample container for receiving and storing the or each collector element and the sample collected thereon for transport and testing. The sample container may be configured to receive and store each collector element after it has been separated or removed from the frame of the sample collection device.

In a preferred embodiment, the sample container holds a medium (e.g., a liquid or gel medium) for eluting the sample from the or each collector element held therein and/or for promoting longevity of the sample for transport and testing. The medium may, for example, be any suitable viral transport medium. Preferably, the sample container has an opening for receiving a frame member of the sample collection device with the collector element thereon, the container being configured for application of a force at a separation point (e.g. via bending or torsion) provided to separate the frame member and the collector element thereon from the frame to harvest the sample collected on the collector element for transport and testing. The container will typically include a closure for covering and sealing the opening. The sample container will preferably be provided with the same unique identifier as the sample collection device; e.g. as a number, code, or the like. In this way, when a sample provided on the harvested collector element/s is received by a laboratory for testing, the laboratory can attribute the sample to the individual to whom that unique identifier has been recorded or registered.

In a preferred embodiment, the sample collection kit includes a unique identifier for use in recording or registering an individual from whom a sample is collected with the sample collection device in the kit. In this way, the unique identifier is designed to support data integrity and sample tracking. The unique identifier may be in the form of a number, a symbol, a code, a signal, or any other form suitable for creating a unique identity for the kit. The unique identifier may be physically provided in or on the sample collection device itself, e.g. in or on the substrate or frame of the device, or in the kit; e.g. in or on packaging.

In a preferred embodiment, the unique identifier is adapted to be recognised or recorded automatically when registering the individual from whom a sample is collected with the sample collection device. In one particular embodiment, the unique identifier is provided in the form of a code (e.g. a QR code) which is able to be scanned or read in an automated way e.g., via QR code-recognition software in a mobile phone application. That code may be provided on the device itself or on the packaging associated with the device. In another particular embodiment, the unique identifier may be in the form of a signal, e.g., a radio-frequency signal via an RFID device, which may be scanned or read in an automated manner. A signal emitter (e.g., RFID) for emitting the unique identifier signal may optionally be provided in or on the sample collection device itself or otherwise in the kit. Once the unique identifier has been scanned or read to record a specific sample collection device, personal details of the individual from whom the sample is collected with that device may then be registered (e.g., name, address, gender, date of birth, health insurance details, etc.) to a database.

According to another aspect, the disclosure provides a sample collection system, comprising a sample collection device or a sample collection kit according to any of the embodiments described above for collecting a nasal sample; and a software application for supporting use of the sample collection device by an individual.

In a preferred embodiment, the software application is accessible or operable via a mobile telecommunications device (herein also simply "mobile device"), like a mobile phone or tablet. In this regard, the software application could optionally be downloaded and installed on the mobile device or alternatively could be accessible online via a web browser. The software application is configured to record or register the sample collection device in association with the individual from whom a sample is to be collected with that device. In this regard, the software application may include code-recognition software for scanning or reading a unique identifier code (e.g., a QR code) provided in association with or on the sample collection device (for example, in the sample collection kit) to record or register that device. The software application will typically also be configured to record personal details (e.g., name, address, gender, date of birth, health insurance details) of the individual. In this way, for example, despite being used at home, the sample collection system enables consistent and reliable data collection in conjunction with consistent and reliable sample collection. The software application comprises a computer program or computer software which is configured to be executed by a computer processor, e.g., microprocessor, as is typically found within a mobile device, such as a mobile phone or a tablet. Of course, the computer program or computer software would also be able to be executed by a personal computer, e.g., a laptop computer, of the individual. The software application may be available to a user online (e.g., via a cloud server) via the Internet as a computer program product to be downloaded or alternatively accessible via an Internet browser.

In a preferred embodiment, the software application provides instruction to the individual via their mobile device on correct use of the sample collection device. These instructions may be available in a number of languages to be selected by the individual and/or may be provided in a schematically illustrative manner which may be understood irrespective of language. The software application may include a timer to provide a means for indicating to the individual when a predetermined sample collection time has elapsed. The timer will typically be started after collector elements of the sample collection device have been introduced into the nostrils of the individual in accordance with the instructions provided. The time may include an alarm which sounds via the mobile device to alert the individual at the end of the predetermined time period for sample collection. This can also operate to record that the individual has complied with the sample collection process. The software application may then provide instructions to the individual on correct harvesting of the collector elements (e.g. separated or removed from a frame of the sample collection device) and for their receipt and storage in the sample container. The individual may note via the software application that harvest of the collector elements is complete (e.g., via a "Done" confirmation or button). As such, the system may automatically record the sample collection as completed in the database. Preferably, the software application could then automatically initiate a delivery of the sample to a laboratory for testing. In this regard, for example, a courier or drone could be dispatched to pick up the sample, or the individual could be provided with a drop-off location/time for dropping off the sample.

According to yet another aspect, the disclosure provides a method of collecting a nasal sample from an individual, the method comprising steps of:

- providing a sample collection device comprising a frame, at least part of which is configured to be received and retained within a nostril of the individual, and a collector provided on and/or carried by said part of the frame for receiving and collecting the nasal sample;
- introducing the collector element provided on and/or carried by said part of the frame into a nostril of the individual, whereby it is received and retained within the nostril such that the collector contacts or engages with an inner surface or tissue of the nostril to receive the sample;
- allowing the collector provided on and/or carried by said part of the frame to remain or reside within the nostril for a predetermined period of time for collection of the sample; and
- removing said part of the frame and the collector provided and/or carried thereon from the nostril to harvest the sample for testing.

In a preferred embodiment, the predetermined period of time for sample collection is at least about 15 seconds, preferably at least about 30 seconds, further preferably at least one or two minutes, and optionally in the range of about 5 minutes to about 8 hours, e.g., in the range of about 15 minutes to about 4 hours. In this regard, the individual typically wears the sample collection device for the predetermined period of time.

In a preferred embodiment, the collector element is introduced into and resides within an anterior nasal cavity, e.g., in the nares or nasal vestibule, to receive and collect the nasal sample for the predetermined period of time.

In a preferred embodiment, the method further comprises separating or removing the collector/collector element from the frame to harvest the sample collected thereon for testing. In a particular preferred embodiment, the collector element may be configured in the form of a sleeve of collector material, and the step of separating or removing the collector element from the frame comprises removing or pulling the sleeve off the frame to harvest the sample collected thereon for testing. In another particular embodiment, the collector element may be fixed to the frame at one or more connection points, and the step of separating or removing the collector element from the frame comprises releasing each connection point, e.g., by application of a suitable force, to harvest the sample for testing. In still a further particular preferred example, the step of separating or removing the collector element from the frame may comprise fracturing or breaking the frame at a position (e.g., a point of weakness) at which the frame is adapted to be broken to harvest the sample collected on the collector element for testing.

In a preferred embodiment, the method comprises accessing and/or operating a software application—preferably via a mobile device, such as a mobile phone or tablet—to support use of the sample collection device by an individual. In this regard, the software application may be downloaded and installed on the mobile device or alternatively may be accessed online via a web browser. The method includes recording or registering the sample collection device in association with the individual from whom a sample is to be collected via the software application. In a particular preferred embodiment, the method includes scanning or reading a unique identifier code (e.g., a QR code) provided on the sample collection device to record or register that device. In this way, for example, despite being used at home, the sample collection system enables consistent and reliable data collection in conjunction with consistent and reliable sample collection.

According to yet another aspect, the present disclosure provides a diagnostic kit, comprising a sample collection device according to any of the embodiments described above for collecting a nasal sample, and a sample test or assay provided in association with the sample collection device.

In a preferred embodiment, the sample test or assay of the diagnostic kit includes a test container for receiving the/each collector element (preferably separated or removed from the frame of the collection device) and the sample collected thereon for testing. In this regard, the test container may preferably have the same or similar features to those of the sample container described above in any one of the embodiments of the sample collection kit.

In a preferred embodiment, the test container holds a first reagent (e.g., optionally in a liquid or gel medium) for interaction with the sample on the or each collector element received therein. To this end, the first reagent may be selected or designed to interact or to react with a target substance or compound in the sample, such as a particular antibody, antigen, cell, protein, and/or nucleic acid to be detected. Thus, the diagnostic kit may, for example, provide an antibody test, an antigen test, or a nucleic acid test for detecting an antibody, antigen, cell, or nucleic acid of interest.

In a preferred embodiment, interaction of the first reagent with a target substance or compound (e.g., a target antibody, target antigen, target cell or target nucleic acid) in the sample is configured to produce an indicator that indicates the presence of that target substance or compound. The indicator may be a sensory indicator, e.g., a visual indicator, such as a colour change or other change in appearance of the reagent or sample, or an olfactory indicator, such as a perceptible smell or odour. In this context, the indicator may require a second reagent, which second reagent may be added to the container following the interaction of the first reagent with the target substance or compound.

In a preferred embodiment, interaction of the first reagent with a target substance or compound (e.g., a target antibody, target antigen, target cell or target nucleic acid) in the sample is configured to produce an electrical potential or polarisation which may be detected by an electrical detector provided in or on the container and/or provided for electrical communication with the reagent or sample.

According to yet a further aspect, the present disclosure provides a diagnostic device, comprising a sample collection device according to any one of the embodiments described above for collecting a nasal sample, and a sample test or assay on the frame or substrate of the sample collection device for testing the sample for presence of a target substance or compound in the sample. As already noted above, the target substance or compound may, for example, be a particular antibody, antigen, cell, protein, or nucleic acid of interest.

In a preferred embodiment, the sample test or assay on the frame or substrate of the sample collection device includes a first reagent for interaction with a sample collected on the or each collector element. The first reagent may be in a liquid or gel medium but may also be provided in a solid form (e.g., as a dry or powdered coating) for contact with the sample on the or each collector element. To this end, the first reagent is typically selected or designed to interact with the target substance or compound in the sample.

In a preferred embodiment, the sample test or assay on the frame or substrate of the sample collection device is in the form of a lateral flow test. As such, the sample test or assay preferably has a lateral flow assay architecture. Alternatively, the sample test or assay on the frame or substrate of the sample collection device may be in the form of vertical flow test; that is, it may include a vertical flow assay architecture.

As noted above, in a preferred embodiment the interaction of the first reagent with a target substance or compound (e.g., target antibody, target antigen, target cell, target protein, or target nucleic acid) in the sample is configured to produce an indicator that indicates the presence of that target substance or target compound in the sample. The indicator may be a visual indicator, such as a colour or other change in appearance.

In an alternative preferred embodiment, interaction of the first reagent with a target substance or target compound (e.g., antibody, antigen, cell, protein, or nucleic acid) in the sample is configured to produce an electrical potential or polarisation which may be detected by an electrical detector provided in or on the substrate or frame of the device. In this regard, for example, the electrical detector may be in the form of a switch or sensor. The switch and/or sensor may preferably be adapted for electrical communication with a mobile telecommunication device.

In view of the ongoing Covid-19 pandemic, the subject of the present disclosure could facilitate quick daily testing (e.g., rapid antigen tests) via a nasal sample which can be utilized at home and could potentially detect a majority of infectious Covid-19 cases. With regard to controlling the Covid-19 pandemic, research indicates that: (i) turnaround time of testing is more important than the sensitivity of the test; (ii) frequency of testing is more important than sensitivity of the test; and (iii) a testing protocol with rapid tests can keep infections closer to zero, even if tests are less sensitive, whereas a slower protocol cannot. Thus, high specificity and speed appear to be more important to managing the Covid-19 pandemic than a hyper-sensitivity of the test.

In this way, the present disclosure desirably provides a diagnostic kit or diagnostic device for a rapid diagnostic test (RDT) using a sample collection device according to any one of the embodiments described above. RDTs are useful for preliminary or emergency medical screening. They also provide a point-of-care test (POCT) for things that formerly needed to be assessed in a laboratory test. Importantly, they can provide same-day results within hours, or even minutes. Examples of RDT include rapid antibody tests, rapid antigen tests, and rapid nucleic acid tests which directly detect the presence or absence of an antibody, antigen, or nucleic acid, respectively. POCTs provide medical diagnostic testing at or near the point of care, i.e. at the time and place of patient care. Thus, a POCT brings the test conveniently to the individual and enables the individual, physician, and care team to receive the test results more quickly, which allows more immediate clinical management decisions to be made.

According to still another aspect, the disclosure provides a diagnostic system, including: a diagnostic device or diagnostic kit according to any one of the embodiments described above, and a software application for supporting use of the diagnostic device or kit by an individual. The software application of this diagnostic system may have the same or similar features as the software application described above in respect of the sample collection system.

The coupling of POCT devices and electronic communication devices enable test results to be shared quickly with government health authorities and care providers. The use of mobile communication devices in the healthcare setting also enables healthcare providers to quickly access test results sent from a POCT device.

BRIEF DESCRIPTION OF THE DRAWINGS

For a more complete understanding of the disclosure and advantages thereof, exemplary embodiments of the disclosure are explained in more detail in the following description with reference to the accompanying drawing figures, in which like reference signs designate like parts and in which.

Figure 1:
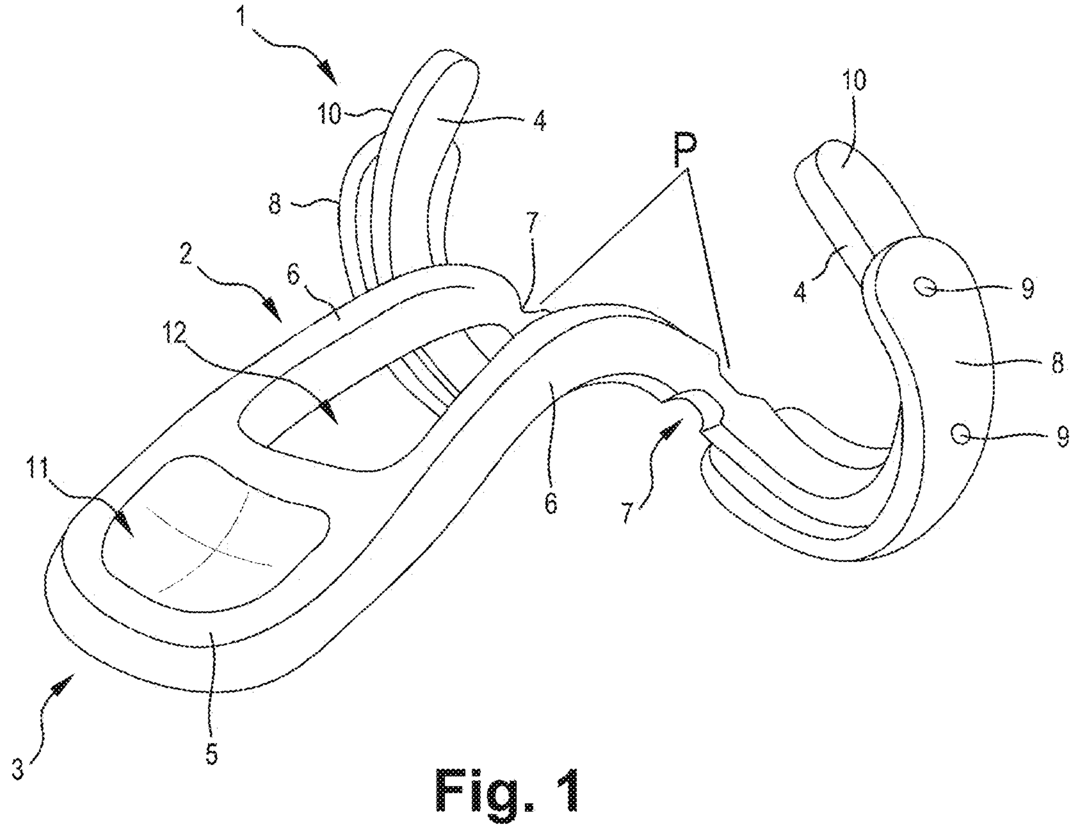
FIG. 1 is a schematic perspective view of a sample collection device according to a first preferred embodiment.

The accompanying drawings are included to provide a further understanding of the present disclosure and are incorporated in and constitute a part of this specification. The drawings illustrate particular embodiments of the disclosure and together with the description serve to explain the principles of this disclosure. Other embodiments and many of the attendant advantages will be readily appreciated as they become better understood with reference to the following detailed description.

It will be appreciated that common and/or well understood elements that may be useful or necessary in a commercially feasible embodiment are not necessarily depicted in order to facilitate a more abstracted view of the embodiments. The elements of the drawings are not necessarily illustrated to scale relative to each other. It will also be understood that certain actions and/or steps in an embodiment of a method may be described or depicted in a particular order of occurrences while those skilled in the art will understand that such specificity with respect to sequence is not actually required.

DETAILED DESCRIPTION OF THE EMBODIMENTS

Referring initially to FIGS. 1 to 4 of the drawings, a first preferred embodiment of a sample collection device 1 for collecting a nasal sample from an individual according to this disclosure is shown in perspective views. The sample collection device 1 comprises a frame 2 formed of a polymer plastic material, such as, for example, polypropylene (PP), polyamide (PA) (Nylon), polyethylene (PE), polystyrene (PS), styrene-ethylene-butylene-styrene (SEBS), or the like. The frame 2 may be formed by moulding and, in this case, is formed as an integral or unitary component. As will be apparent from FIGS. 1 to 4, the frame 2 of the device 1 comprises a central portion 3 and two cantilevered frame members 4 in the form of ribs which are curved or arcuate (like "cow horns") and extend laterally outwardly in opposite directions from the central portion 3. The central portion 3 is part of the frame 2 which, in use, is configured or designed to remain largely outside or external to the nostrils. The central portion 3 comprises a generally U-shaped body having a tab part 5 and two frame members 6 in the form of stems or legs extending roughly parallel to one another from the tab part 5 towards and into connection with a respective one of the lateral curved rib members 4. As is apparent from FIG. 1 and FIG. 3, each of the leg members 6 of frame 2 interconnects with the respective rib member 4 at a necked or notched region 7 of reduced thickness. This necked or notched region 7 thus forms a point of weakness or fracture point P, the purpose of which will be described shortly.

Figure 3:
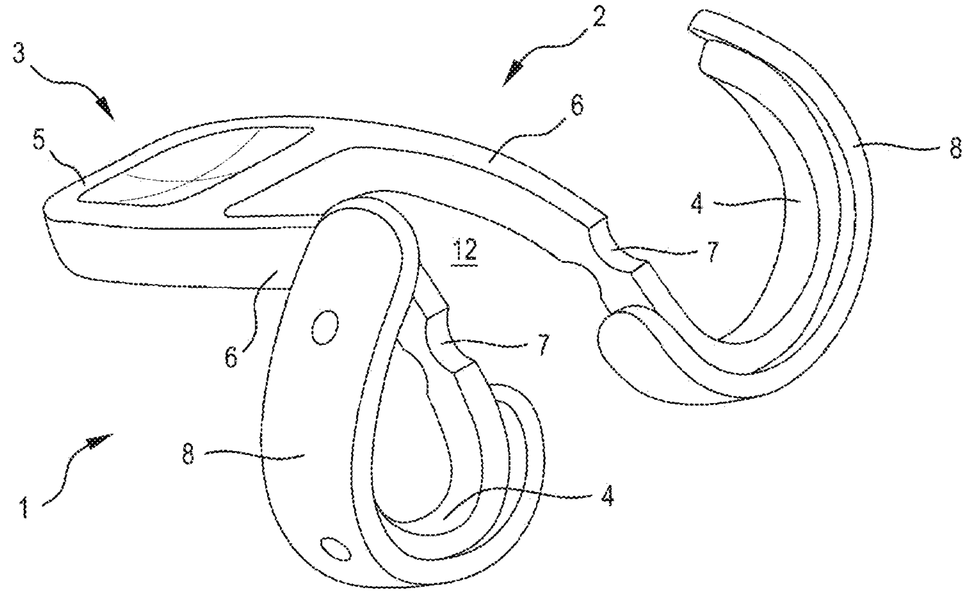
FIG. 3 is a perspective view of a sample collection device according to the first preferred embodiment.

With further reference to FIG. 1 and FIG. 3 of the drawings, the sample collection device 1 further comprises a collector element 8 in the form of a pad of fibrous collector material provided on and carried by each of the curved rib members 4. Each collector pad 8 may be comprised of e.g., cotton, rayon, calcium alginate, polyester, polyamide (e.g., Nylon), polypropylene, or polyethylene and is designed for receiving a liquid or semi-solid nasal sample, typically in the form of a mucosal excretion. That is, each pad 8 is adapted to absorb nasal mucus in order to collect the sample. Each collector pad 8 is connected to a respective one of the rib members 4 at connection points 9 by bonding, fusing, or a connection element, such as a pin connector. Furthermore, each pad 8 extends along a surface or side 10 of the rib member 4 that, in use, is configured to face the tissue of the nasal cavity. For this reason, the collector pads 8 are also soft for comfort within the nostril during use.

In this regard, it will be appreciated that the pair of rib members 4 with their respective collector pads 8 are configured to be inserted or introduced into the nostrils of an individual for collecting a nasal sample. To this end, the rib members 4 are designed to be relatively soft and resiliently flexible or 'springy' to assist their easy insertion into the nostrils. Similarly, the collector pads 8 are relatively soft to promote user comfort. The tab part 5 of the central portion 3 forms a handle member for the individual to grasp and to manipulate the device 1 during insertion of the rib members 4 and collector pads 8 into the nose. As will be understood, it is important for the user to avoid touching the collector pads 8 with his/her hands to avoid any potential cross-contamination of the sample. The individual therefore grasps the device via the tab part 5 of the central portion 3, which may include a curved depression 11 to promote gripping with a finger or thumb. The stem or leg members 6 extending from the tab part 5, and a gap 12 between leg members 6, enable the respective ribs 4 and collector pads 8 to be inserted into the nostrils on either side of the septum. In this way, the rib members 4 and the collector pads 8 can be positioned and retained or accommodated within a lower nasal cavity for collection of a sample via the pads 8. The collector pads 8 provided on the flexible rib members 4 conform to and complement a surface profile or curvature of the nasal cavity.

In use, therefore, the U-shaped body of the central portion 3 of sample collection device 1 is arranged to span a septum of a nose when worn by an individual, with the leg members 6 extending into each nostril on either side of the septum. The leg members 6 may be inclined somewhat towards each other such that a relatively greater distance is provided between the leg members 6 at the tab part 5 to accommodate the columella of the nose when worn by the individual. The distal end regions of the leg members 6 may, in use, be arranged to engage with the septum and extend from the septum behind the columella and alar fibrofatty tissue of the nose, thereby allowing the rib members 4 on which the collector elements 8 are carried, in use, to extend along respective nasal orifices to an inner wall of the nostrils.

Figure 2:
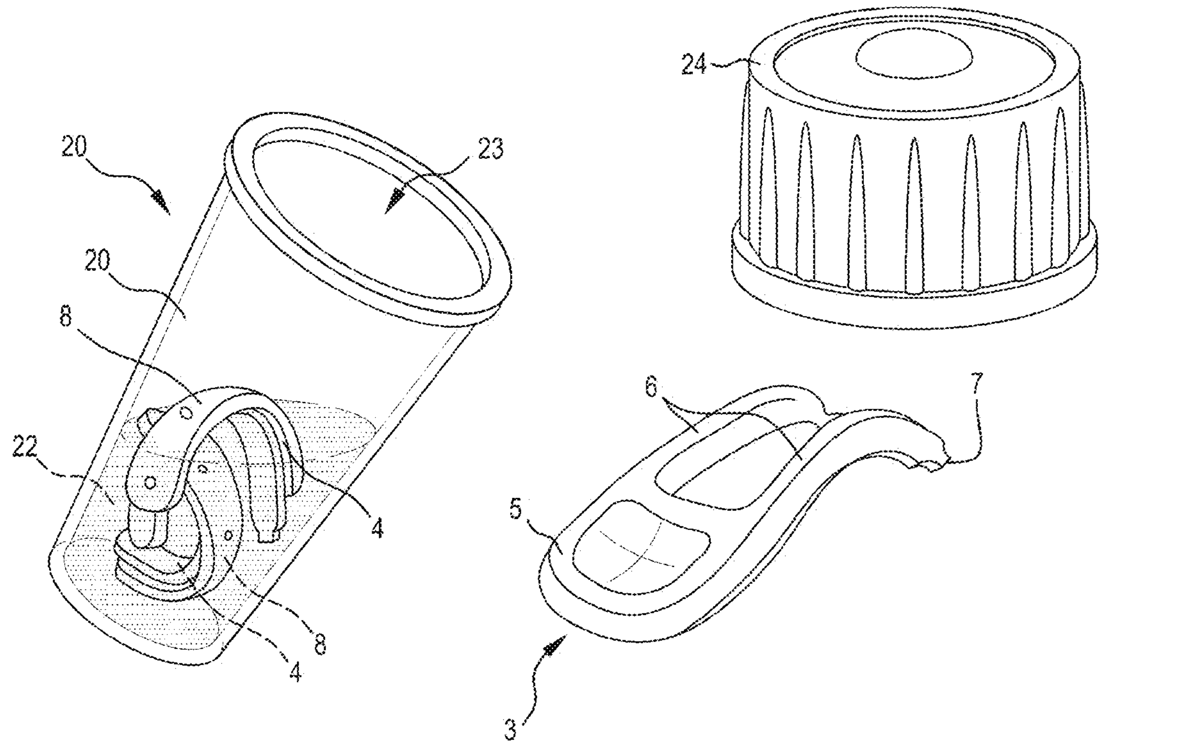
FIG. 2 is a schematic perspective view of a sample collection kit including the sample collection device of FIG. 1.
Figure 4:
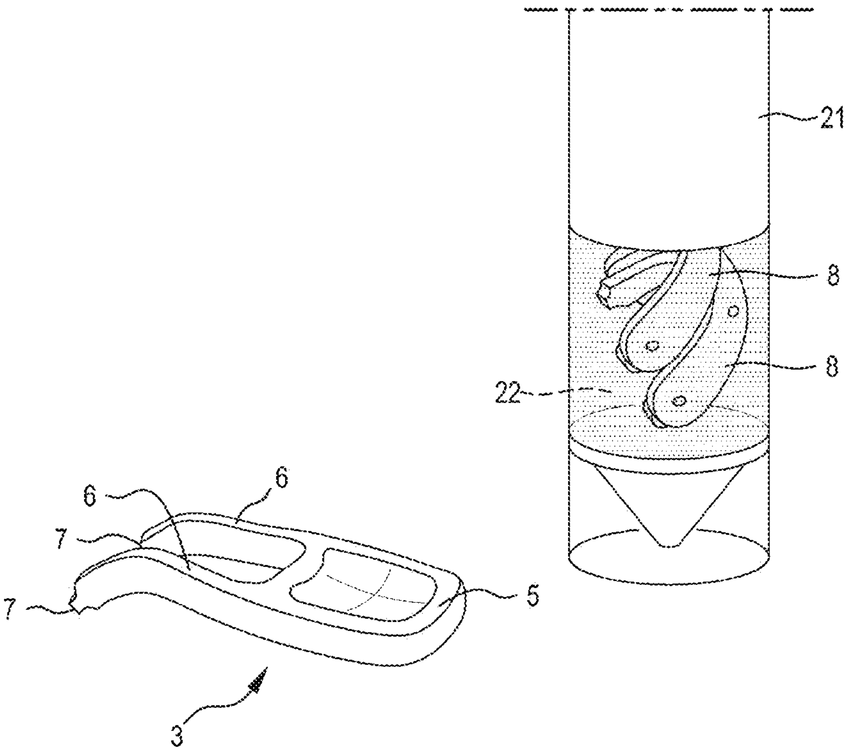
FIG. 4 is a perspective view of a sample collection kit incorporating the sample collection device of FIG. 3.
Figure 5:
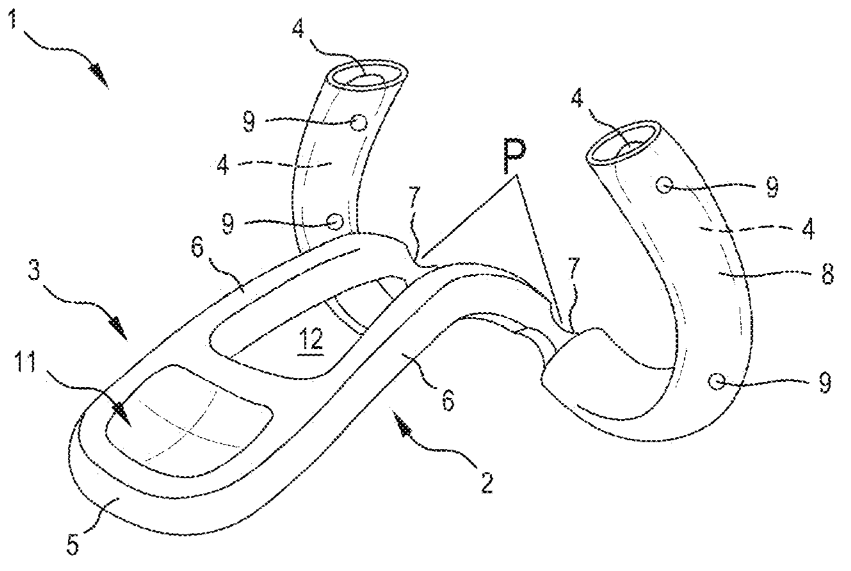
FIG. 5 is a schematic perspective view of a sample collection device according to a second preferred embodiment.
Figure 6:
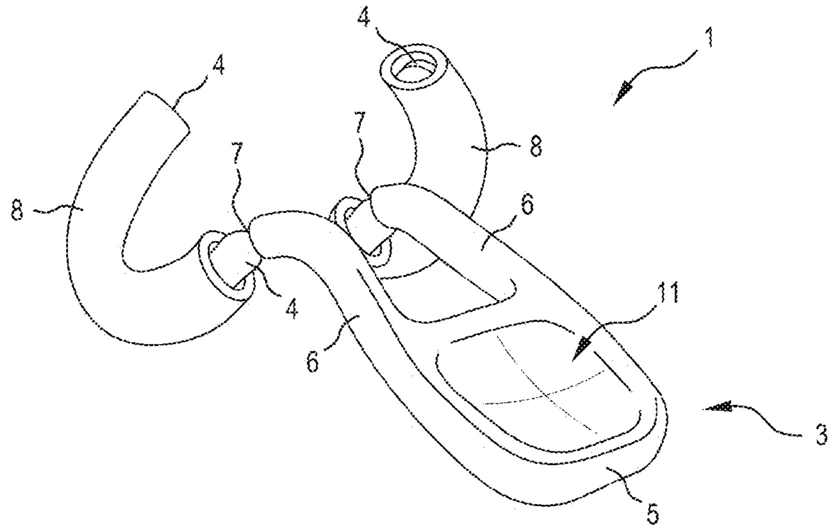
FIG. 6 is a perspective view of a sample collection device according to the second preferred embodiment.
Figure 7:
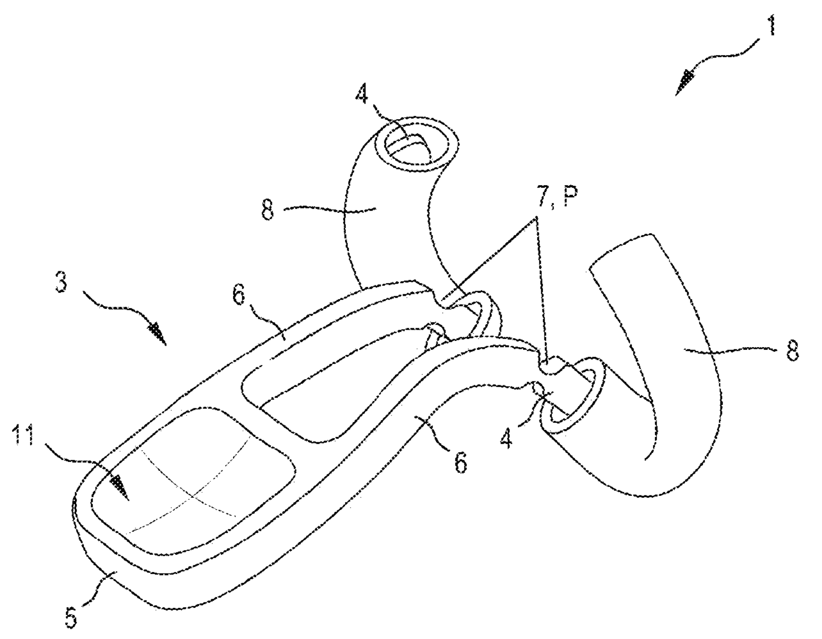
FIG. 7 is another perspective view of the sample collection device shown in FIG. 6.

After the rib members 4 and the collector pads 8 of sample collection device 1 are introduced and accommodated in the nostrils of the individual, they remain or reside there for an extended or predetermined sample collection time of at least about 15 secs, and typically in a range of about 15 minutes to several hours. For example, the individual may wear the sample collection device 1 during the day or in the night (e.g., while he/she sleeps) during collection of the sample via the pads 8. After the predetermined period of time for sample collection has elapsed, the user may then remove the rib members 4 and collector pads 8 from the nose by grasping the handle or tab part 5 and gently withdrawing those parts of the device 1 from the nostrils. As can be seen in FIGS. 2 and 4, a sample collection kit 20 according to a preferred embodiment comprises the sample collection device 1 and a container or vial 21 for receiving and storing the collector pads 8. To this end, the container or vial 21 contains a liquid or gel medium 22 for eluting the biological sample from each collector pad 8 and for promoting longevity of the sample for transport and testing. To harvest each of the collector pads 8, each of the rib members 4 may be respectively inserted, in turn, into an upper opening 23 of the vial 21 by the individual holding the device 1 by the handle or tab part 5. A bending or torsional force is then manually applied by the individual to the fracture point P at the necked or notched region 7 to break the rib member 4, and the collector pad 8 carried on it, from the respective leg member 6 of the frame 2, so that the rib member 4 and its collector pad 8 are separated from the frame 2 and drop into the medium 22. The same is then performed with the other rib member 4, to achieve the situation shown in FIG. 2 and FIG. 4. A cap or closure 24 is then applied to cover and seal the container or vial 21, which is then ready for transport to a laboratory for testing.

Figure 8:
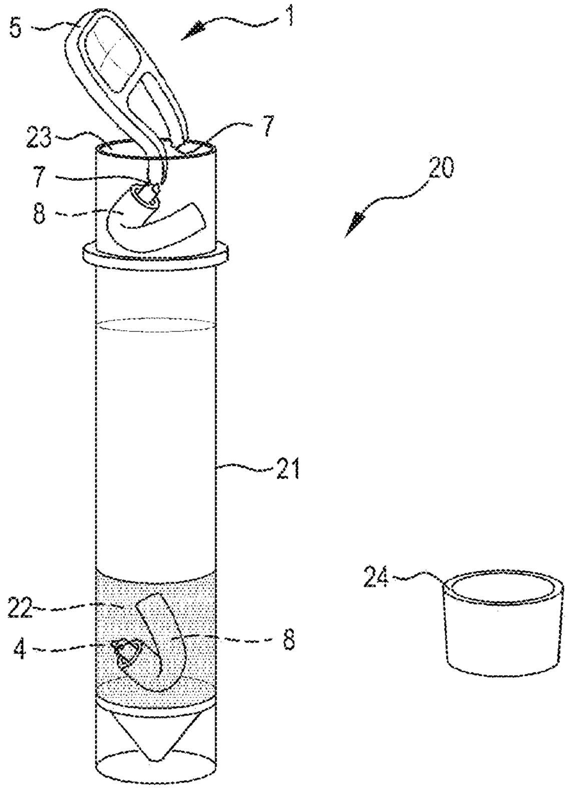
FIG. 8 is a perspective view of a sample collection kit according to an embodiment and incorporating the sample collection device of FIGS. 6 and 7.

With reference now to drawing FIGS. 5 to 8, a second preferred embodiment of a sample collection device 1 for collecting a nasal sample from an individual according to the disclosure is shown in range of perspective views. The general structure of the sample collecting device 1 in this embodiment is essentially the same as in the first embodiment, so a description of that structure will not be repeated, but like reference characters in the drawings identify like parts. A difference in this second embodiment, however, concerns the collector elements 8 which are provided in the form of tubular sleeves, which surround or sheathe the curved rib members 4, instead of the pads shown in FIGS. 1 to 4. In this embodiment, the collector sleeves 8 may be knitted sleeves comprised of fibres of e.g. cotton, rayon, calcium alginate, polyester, polypropylene, or polyethylene, or may also be foam sleeve elements comprised of e.g. a urethane foam. The collector sleeves 8 may be form-fitted or friction fitted on the flexible rib members 4 or they may optionally again be connected to the rib members 4 via connection points 9, e.g., by bonding, fusing, or a connection element, like a pin connector. Use and operation of the sample collection device 1 of the second embodiment correspond to the use and operation described above for the first embodiment, including for the harvesting of the collector sleeves 8 in a vial or container 21 of a sample collection kit 20, as shown in FIG. 8. As an alternative, however, the collector sleeves 8 of this embodiment could be pulled or drawn off the ends of the rib members 4 and placed in the medium 22 within the vial or container 21 of a collection kit 20. To this end, an instrument or tool, such as tweezers (not shown), may be provided so that the user need not touch (and potentially contaminate) the collector sleeves 8 in this process.

Figure 9:
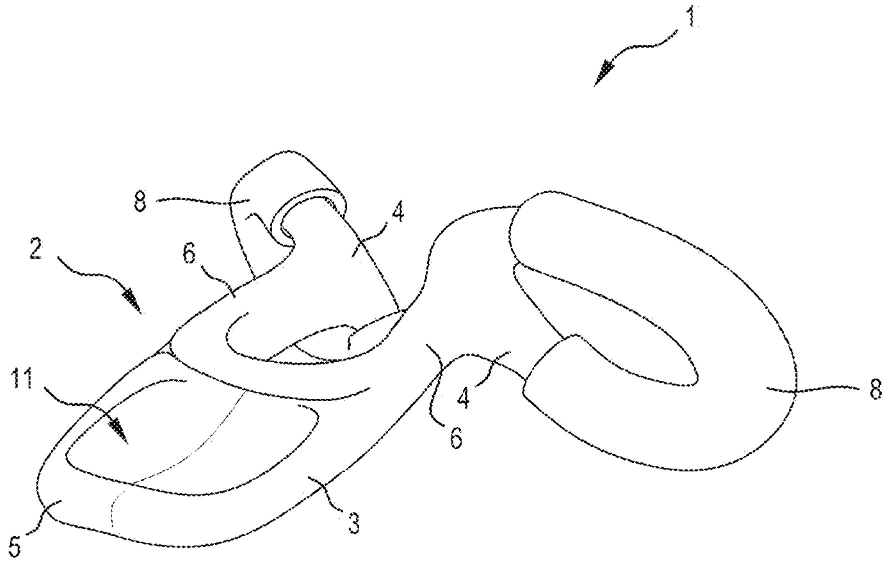
FIG. 9 is a schematic perspective view of a sample collection device according to a third preferred embodiment.
Figure 10:
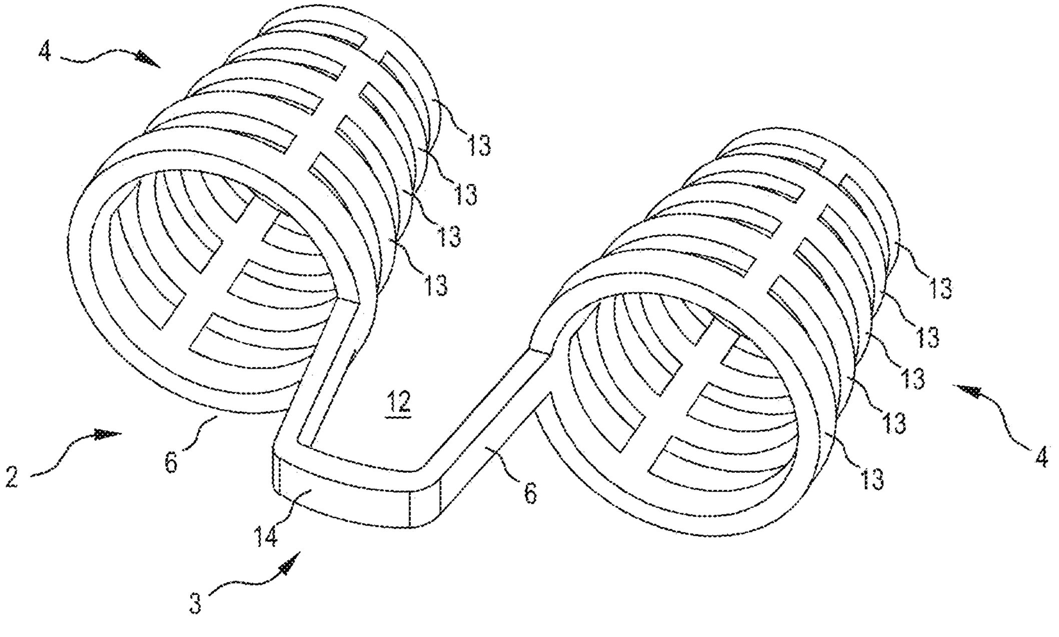
FIG. 10 is a perspective view of a sample collection device according to a fourth preferred embodiment.
Figure 11:
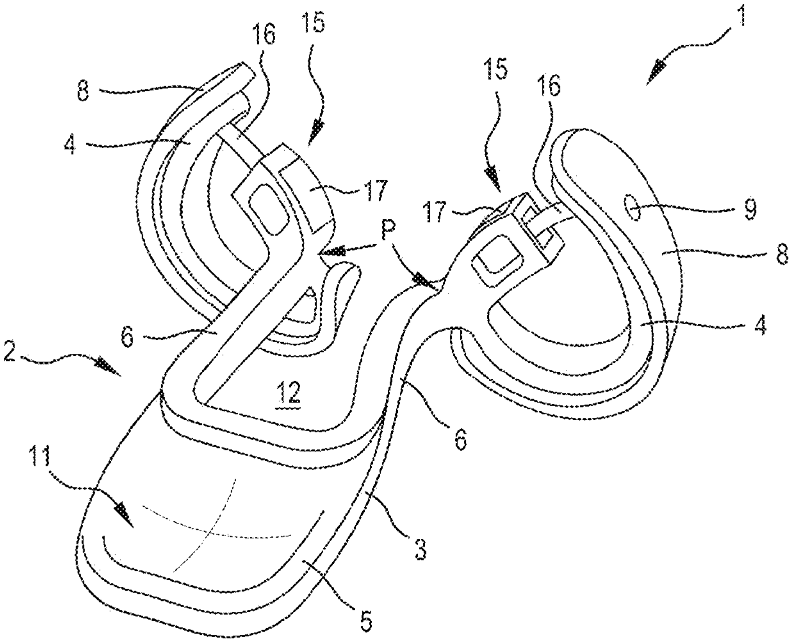
FIG. 11 is a perspective view of a sample collection device according to a fifth preferred embodiment.

FIGS. 9, 10 and 11 of the drawings illustrate a number of alternative embodiments of a sample collection device 1 that exhibit differences in the configuration of the frame 2. Again, however, it will be noted that the general use of these sample collection devices 1 corresponds to the use as it has been described above for the first embodiment. In the third embodiment of FIG. 9, the frame members 4 upon which the collector elements 8 are provided or carried are in the form of rings or closed loops. Similarly with the second embodiment of FIGS. 5 to 8, the collector elements 8 are provided in the form of sleeves which surround or sheathe the loop members 4. Although not shown in FIG. 9, a fracture point P may be provided via a necked or notched region at a junction between each loop member 4 and the respective leg member 6 to which it is attached. As an alternative, the sleeve-like collector elements 8 could include a frangible seam which, upon application of a pulling force to the sleeves 8 (e.g., via instrument or tool, such as tweezers), then ruptures enabling the collector sleeves 8 to be removed from the loop members 4 for placement in a vial or container 21 of a sample collection kit 20. In a fourth embodiment shown in FIG. 10, the frame members 4 upon which the respective collector elements (not shown) are to be supported are provided in the form of a series of interconnected loops or hoops 13, which form a cage structure. The collector elements 8 in this case could be provided in the form of a cylindrical or conical sheath or sleeve for covering an outside or outer periphery of the cage structure. This structure results in the collector elements (not shown), in use, extending further or deeper into the nasal cavity. In this embodiment, also, the tab part 5 is missing and the central portion 3 comprises a simple band 14 which interconnects the leg members 6. The band 14 could nevertheless still operate as a crude handle or gripping portion for a user to manually manipulate the device.

In the fifth embodiment shown in FIG. 11, the sample collection device 1 includes a frame 2 having a very similar configuration to that of the first embodiment. The collector elements 8 are also provided in the form of pads for absorbing and retaining the sample, as in the first embodiment. In this fifth embodiment, however, each rib member 4 includes an adjuster 15 for setting or adjusting a radial position of the collector pad 8. In this regard, the adjuster 15 preferably comprises a mechanism, e.g., a ratchet mechanism, for setting or adjusting a curvature or radial extent of the respective rib member 4 and, thus, also of the associated collector pad 8. In this embodiment, for example, each of the adjuster mechanisms 15 comprises a pin 16 and a socket 17 arranged to receive and engage with the pin 16. The pin 16 may include a series of ridges or teeth (as will be understood in the art) for engaging with the socket 17 as the pin 16 is progressively inserted to set or fix a desired position. An enlargement or head may be provided at an end of the pin 16 to prevent the pin withdrawing from the socket 17. In this regard, a shoulder provided inside the socket 17 may be configured to engage with the enlargement or head of the pin 16 to prevent the pin from withdrawing from the socket. This may allow some pre-adjustment of the shape and/or position of the rib members 4 and the collector pads 8 prior to insertion of those parts of the device 1 into the individual's nostrils for sample collection.

Figure 12:
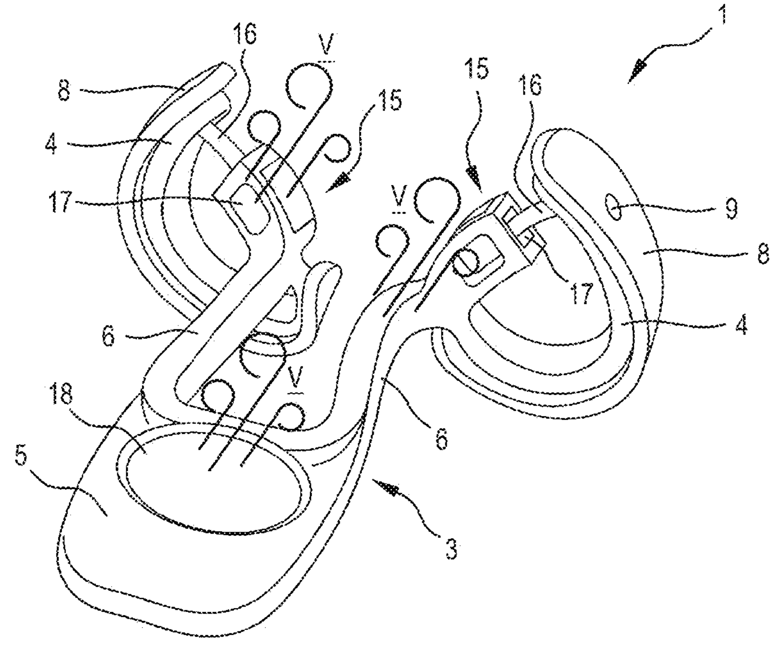
FIG. 12 is a perspective view of a sample collection device according to a sixth preferred embodiment.

With reference now to FIG. 12 of the drawings, a sixth embodiment of a sample collection device 1 is illustrated. This sixth embodiment corresponds substantially to the embodiment of FIG. 11, except that it further includes a sample collection accelerator 18 to promote excretion of nasal mucus. The accelerator 18 comprises a pad impregnated with a substance for inhalation by the individual to promote the excretion of nasal mucus. In this way, the pad 18 provides a source of the accelerator substance and it is supported on the central portion 3 of the frame 2, which, in use, is positioned adjacent the individual's nostrils when the rib members 4 and respective collector pads 8 are accommodated or retained within the nostrils. The accelerator 18 emits the substance in the form of fumes, vapour, or volatiles V which, upon inhalation, promote excretion of nasal mucus and thus operate to reduce the predetermined time period for sample collection. This feature of the accelerator 18 may be included in any of the other embodiments.

Figure 13:
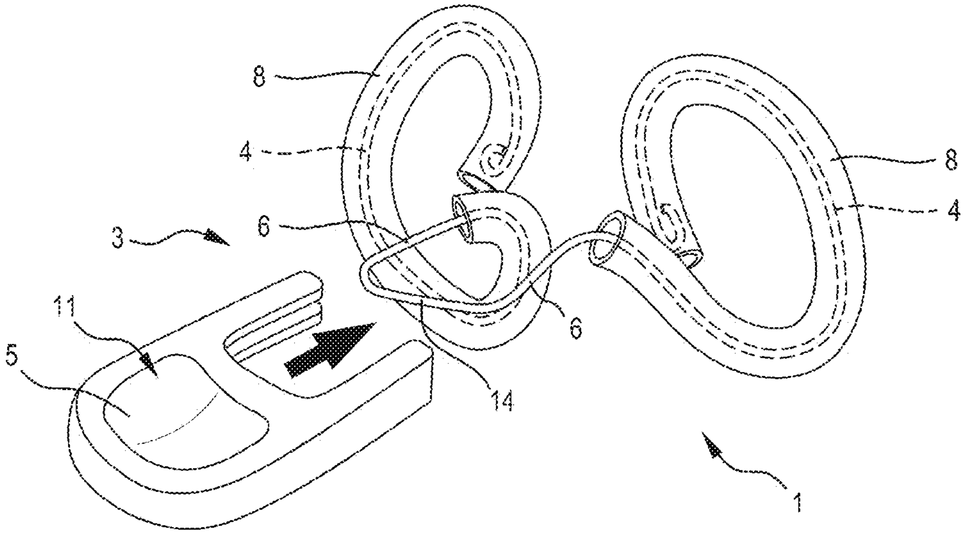
FIG. 13 is a schematic perspective view of a sample collection device according to a seventh preferred embodiment.
Figure 14:
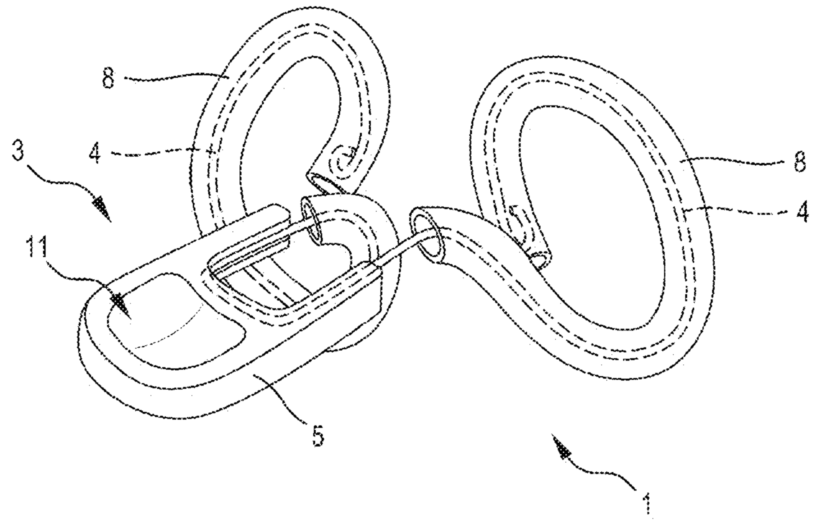
FIG. 14 is another schematic perspective view of the sample collection device in FIG. 13.

With reference to further FIGS. 13 and 14 of the drawings, a seventh preferred embodiment of a sample collection device 1 is shown schematically. In this embodiment, the frame 2 of the device 1 is comprised of a metal wire. The wire is shaped to provide a U-shaped central portion 3 and a pair of frame members 4 in the form of ribs which are curved or arcuate and extend laterally outwardly in opposite directions from the central portion 3. Again, the curved rib members 4 are resiliently flexible and 'springy' for ready adaptation to the size and shape of the nasal cavity of the individual, thereby promoting wearer comfort. In this example, the collector elements 8 are again provided in the form sleeves which surround or sheathe the rib members 4. The central portion 3 of this embodiment includes a removable tab part or handle 5, preferably formed of plastic, which is designed to clip onto two roughly parallel extending wire leg members 6 and a connecting wire band 14 of the central portion 3 interconnecting the two rib members 4. The fact that the tab part or handle 5 is removable makes the sample collection device 1 considerably less obtrusive when it is being worn by the user, e.g. when sleeping. Further, because tab part or handle 5 can be removed, harvesting collector sleeves 8 after the predetermined time period for sample collection has elapsed may simply involve placing the wire part of the frame 2 with the collector sleeves 8 thereon into the container or vial 21 of the collection kit 20 for transport to the laboratory for testing.

Figure 15:
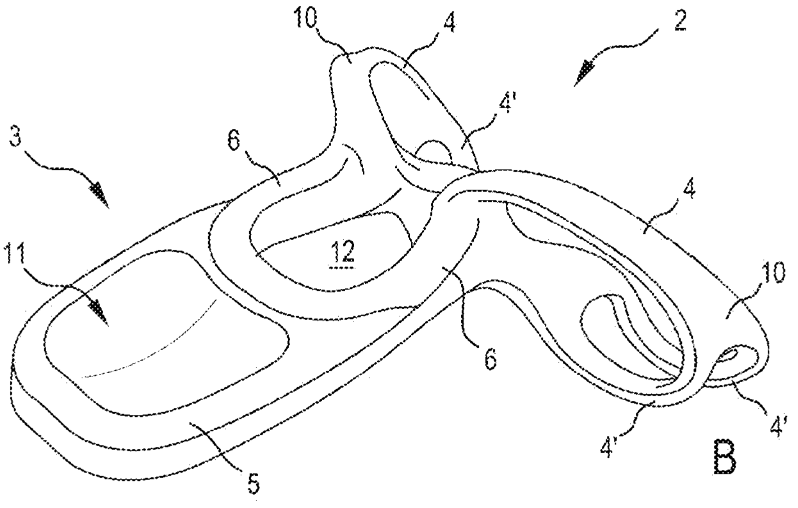
FIG. 15 is a perspective view of a frame of a sample collection device according to an eighth preferred embodiment.
Figure 16:
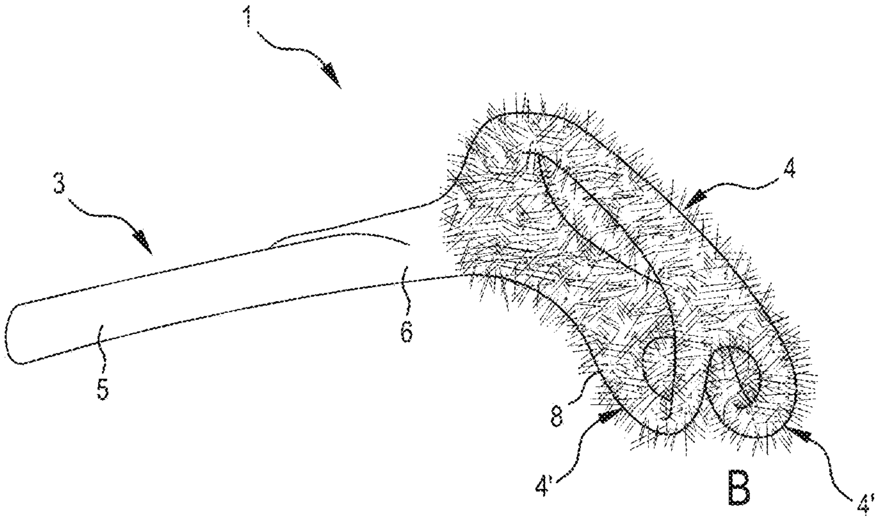
FIG. 16 is a side view of the sample collection device of the embodiment in FIG. 15.
Figure 17:
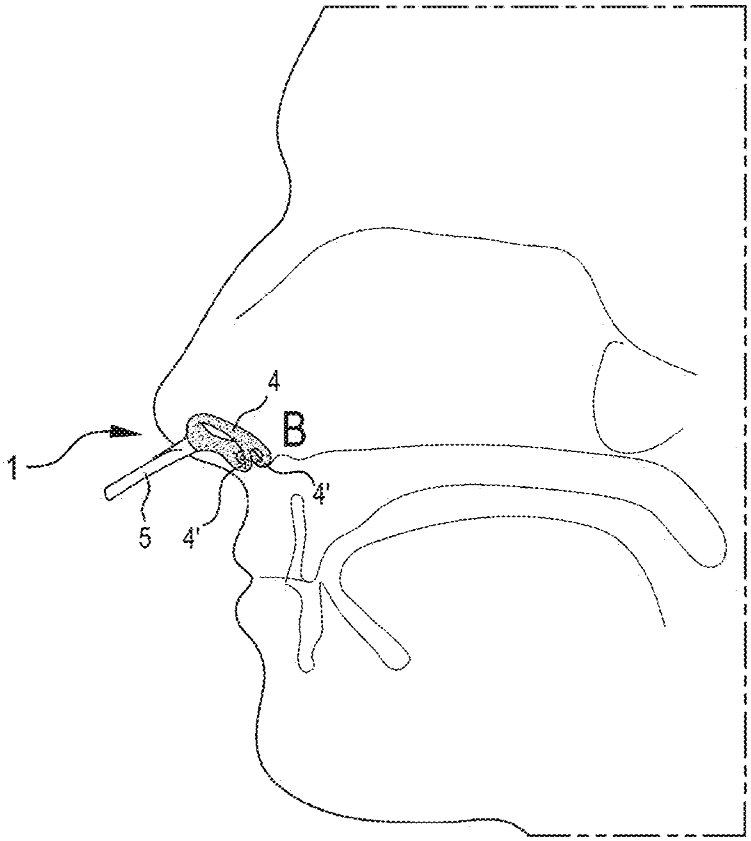
FIG. 17 is a schematic illustration of the sample collection device of FIG. 16 in use.

Referring now to drawing FIGS. 15 to 17, an eighth preferred embodiment of a sample collection device 1 is illustrated. As can be seen in FIG. 15, the central portion 3 of the frame 2 is very similar in configuration to the previous embodiments and includes a generally U-shaped body having a tab part 5 forming a handle and a pair of leg members or stems 6 extending therefrom. The rib members 4 in this embodiment are somewhat different, however. Each elongate rib member 4 has looped profile or forms a closed loop which approximates an ellipse and enables the rib member 4 to be received and to seat within the nostril comfortably and consistently in the nasal vestibule, as seen in FIG. 17, which is important for achieving consistency both in use and in sample collection. Further, each rib member 4 on which the collector 8 is provided/carried in form of a layer of fibres, especially flocked fibres, is configured broader or wider in a region B thereof to be located deeper within the nasal cavity or nares. In this way, the rib member 4 provides a larger surface area for bringing the collector 8 carried thereon into contact with the surface of the nares or nasal cavity likely to provide greater sample load for collection. For similar reasons, the rib member 4 is open, splayed or divided into riblets 4' in this region to provide greater surface area for supporting the collector fibres 8', e.g., flocked fibres, of the collector 8, to increase a potential sample load.

Figure 18:
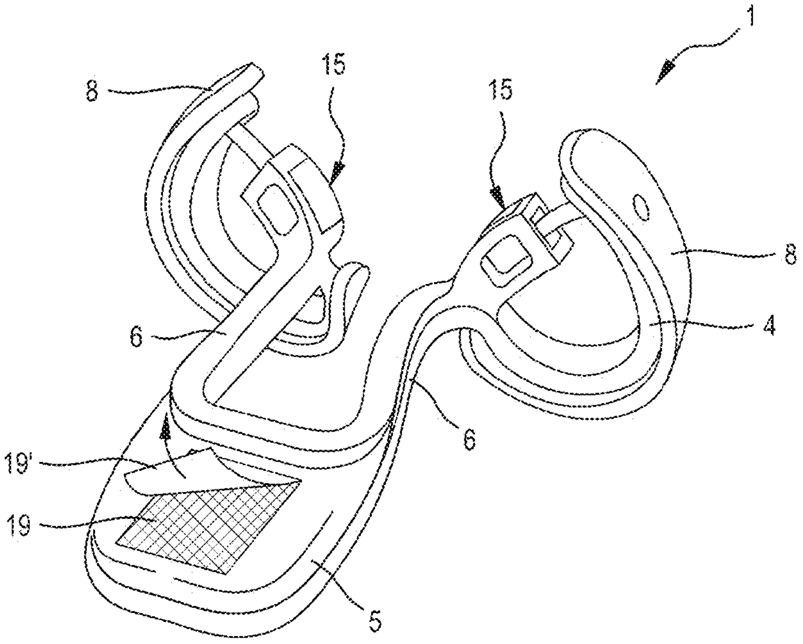
FIG. 18 is a perspective view of a sample collection device according to a ninth preferred embodiment.

Further, with reference now to FIG. 18, a ninth embodiment of a sample collection device 1 is shown. This embodiment corresponds substantially to the fifth embodiment of FIG. 11 but includes a timing indicator 19 for indicating to the individual or wearer when a predetermined time period for sample collection has elapsed. The indicator 19 is provided on the tab part 5 of the frame 2 that remains external of the nostrils, and therefore visible, during use of the device 1. The timing indicator 19 comprises a patch that is adapted to change appearance (e.g., change colour) over time. In this regard, the indicator patch 19 includes a substance selected to react with air and/or light over the predetermined time period in order to change colour over that time. Upon commencing use of the device 1, therefore, the indicator patch 19 may be initially exposed to air and/or light by removing a protective cover or label 19'. After the predetermined time for sample collection has elapsed, the indicator patch 19 will have changed colour due to exposure to air and/or light and will indicate to the user or wearer that the sample collection device 1 can now be removed. In this way, the device 1 is designed to achieve consistency of use by individuals testing themselves. This feature of the timing indicator 19 may be included in any of the other embodiments described herein.

Figure 19:
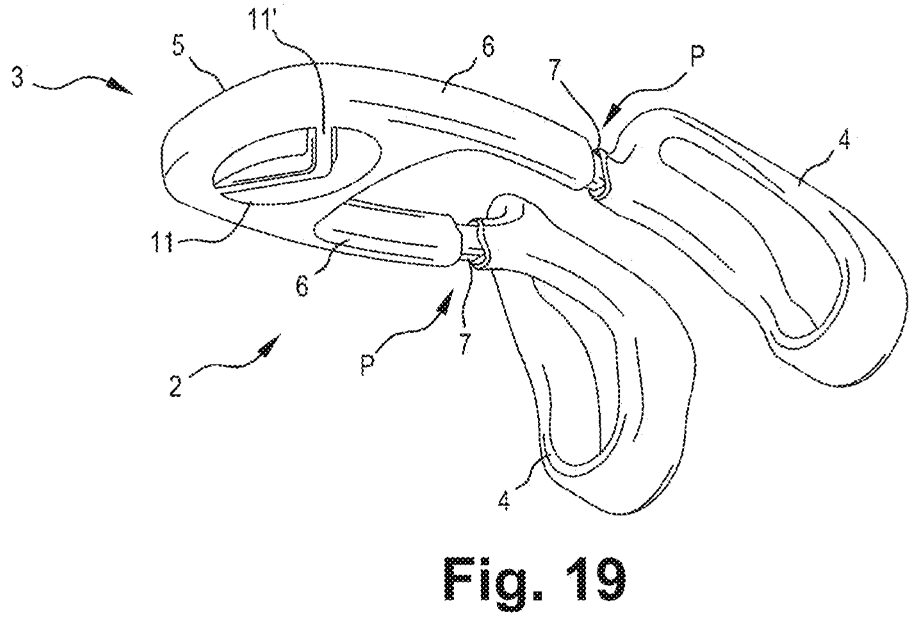
FIG. 19 is a perspective view of a frame of a sample collection device according to a tenth preferred embodiment.
Figure 20:
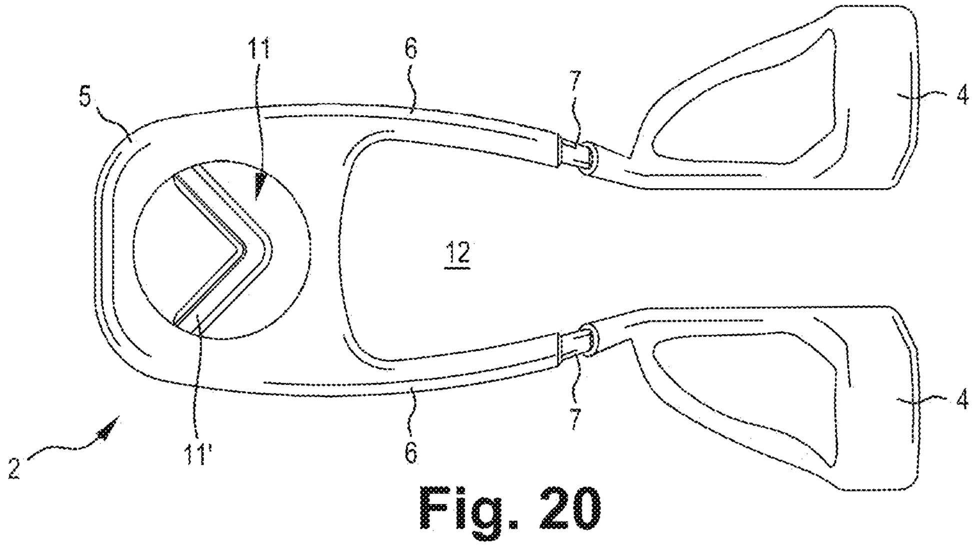
FIG. 20 is an underside view of the frame of a sample collection device shown in FIG. 19.
Figure 21:
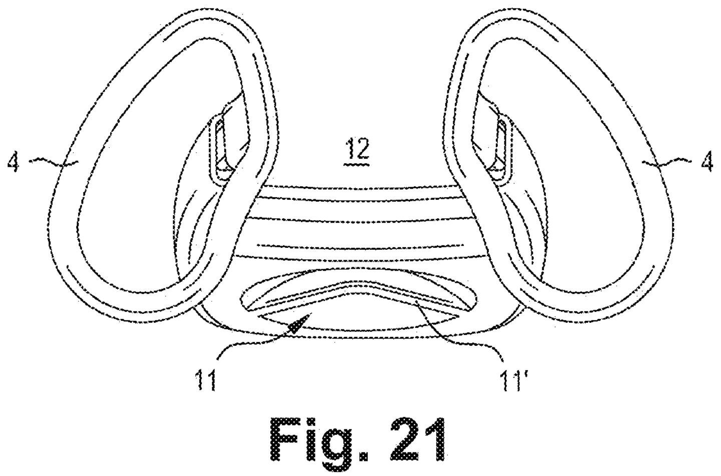
FIG. 21 is a rear view of the frame of a sample collection device shown in FIG. 19.
Figure 22:
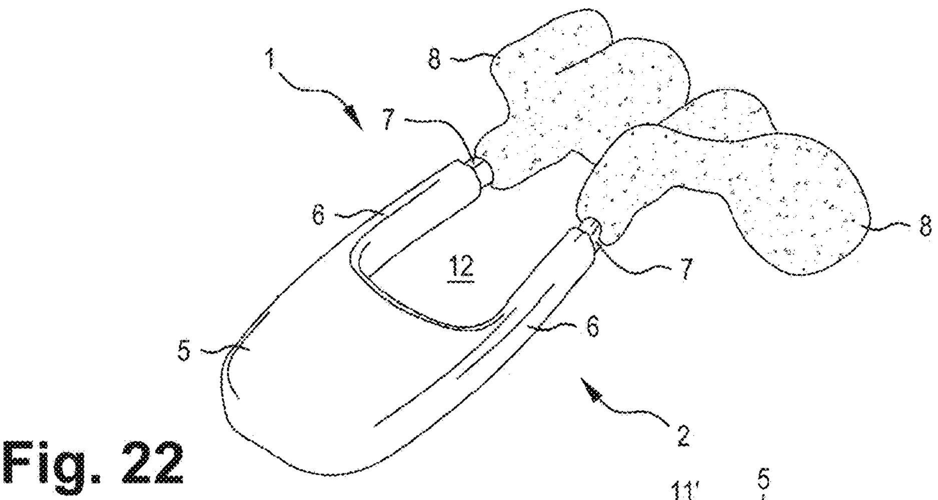
FIG. 22 is a top perspective view of the sample collection device according to the tenth preferred embodiment.
Figure 23:
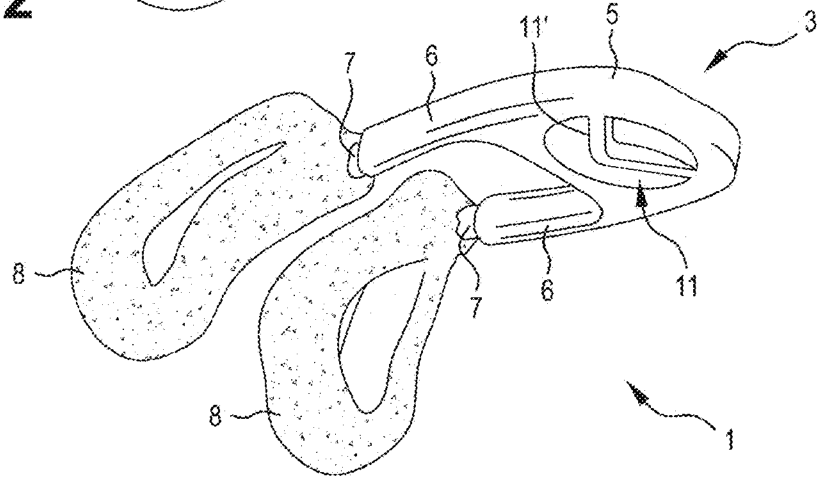
FIG. 23 is a bottom perspective view of the sample collection device in FIG. 22.
Figure 24:
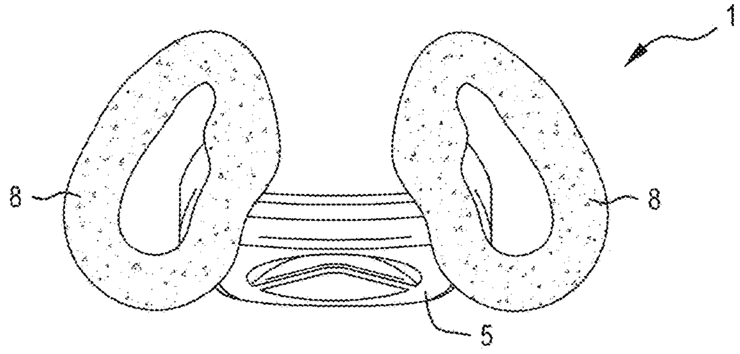
FIG. 24 is a rear view of the sample collection device in FIG. 22.
Figure 25:
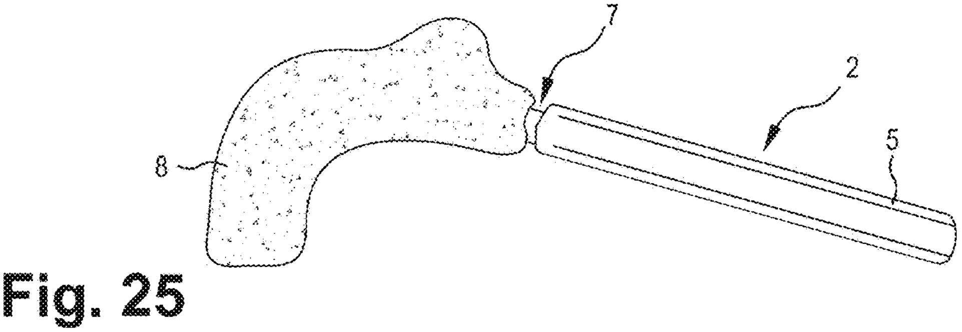
FIG. 25 is a side view of the sample collection device in FIG. 22 and FIG. 23.

Referring to drawing FIGS. 19 to 21, a tenth embodiment of a frame 2 of a sample collection device 1 is shown in various views, and the sample collection device 1 itself is shown in FIGS. 22 to 25. The frame 2 of this embodiment incorporates many of the same basic features as the other embodiments described above. For example, the frame 2 again includes a central portion 3 in the general form of a U-shaped body and two looped frame members 4 which extend rearwardly and laterally to opposite sides of the central portion 3. The central portion 3 has a generally U-shaped body with a tab part 5 that forms a handle for an individual to grip, hold and/or manipulate the device 1 during use, and two frame members 6 in the form of stems or legs extending roughly parallel to one another from the tab part 5 towards and into connection with a respective one of two lateral loop-shaped frame members 4. That is, as is apparent from FIGS. 19 to 21, each of the stems or leg members 6 of the frame 2 interconnects with a respective loop member 4 at a necked or notched region 7 of reduced thickness, which forms a point of weakness or a fracture point P, as described above.

Each of the loop-shaped frame members 4 (i.e., rib members) is configured or adapted to carry or support a collector element 8 for receiving and collecting a nasal sample, as shown in drawing FIGS. 22 to 25. In this embodiment, the respective collector elements 8 comprise a surface covering of fibres 8', such as flocked fibres, provided over each of the looped frame members 4 for absorbing the sample. The flocked fibres 8' may be adhesively applied via an electrostatic deposition technique to provide the fibre layer or covering forming each of the collector elements 8 on the respective looped frame members 4. In this regard, it will be noted that the looped frame members 4 are completely obscured by the thick layer of flocked fibres forming the collector elements 8. It will also be noted that the tab part 5 of the central portion 3 in the frame 2 of this tenth embodiment includes a recess or depression 11 on its underside to promote gripping with the thumb. This position of the recess or depression 11 on the underside of the tab 5 promotes ease and comfort in use. The tab 5 also includes a haptically perceptible marker (i.e., an arrowhead) 11' on the underside (e.g., in the recess 11) to assist an individual in the correct orientation of the sample collection device 1, and also to indicate the direction of introduction into the nostrils by the user.

Figure 26A:
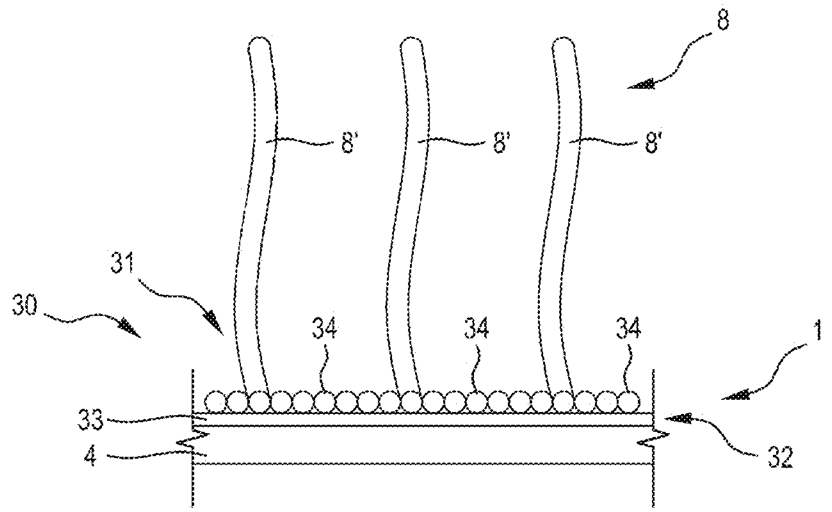
FIG. 26*a* is a schematic close-up side view of part of a collector element of a diagnostic device according to a preferred embodiment.
Figure 26B:
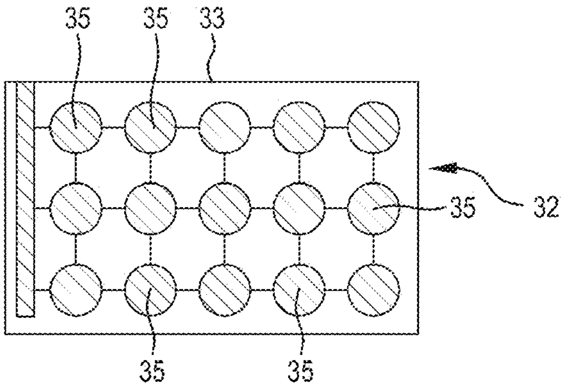
FIG. 26*b* and FIG. 26*c* are schematic plan views of lateral flow assay architectures in a sample test of a diagnostic device according to preferred embodiments.
Figure 26C:
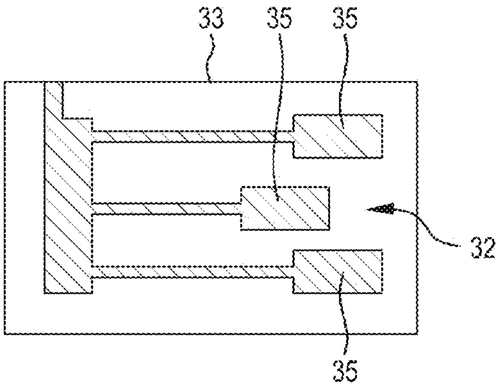

With reference now to FIGS. **26*a* to 26*c* of the drawings, an embodiment of a diagnostic device 30 is illustrated. The diagnostic device 30 includes a sample collection device 1 for collecting a nasal sample comprising a frame 2 with a central portion 3 and rib members 4 carrying collector pads 8 of flocked fibres 8', as per each or any of the embodiments described above. In the close-up view of FIG. 26*a*, the individual fibres 8' or fibre flocking 8' of the collector pad 8 can be seen. The diagnostic device 30 further includes a sample test or assay 31 provided on the frame 2 in the form of a lateral flow assay architecture 32 for testing the sample collected by each pad 8 for the presence of a target substance or compound, such as a particular antibody, antigen, cell, protein or nucleic acid of interest. A reagent 34 is provided or carried on a substrate 33 of the test or assay 31 within or adjacent to the collector pad 8. With reference to FIGS. 26***b* and 26*c*, variations of the substrate 33 in two different lateral flow assay architectures are shown. In each case, the lateral flow assay architecture promotes the transmission or flow of a collected sample via capillary action between patches 35 of the assay architecture on the test substrate 33 for interaction with the reagent 34. A resultant interaction of the reagent 34 with the target substance or compound in the sample is designed to produce a visual indication, such as a colour change in the reagent or sample, denoting the presence of the target substance or compound in the sample. As will be appreciated, a person skilled in the art can select the desired reagent 34 in light of the target substance or compound to be detected or identified.

Figure 27:
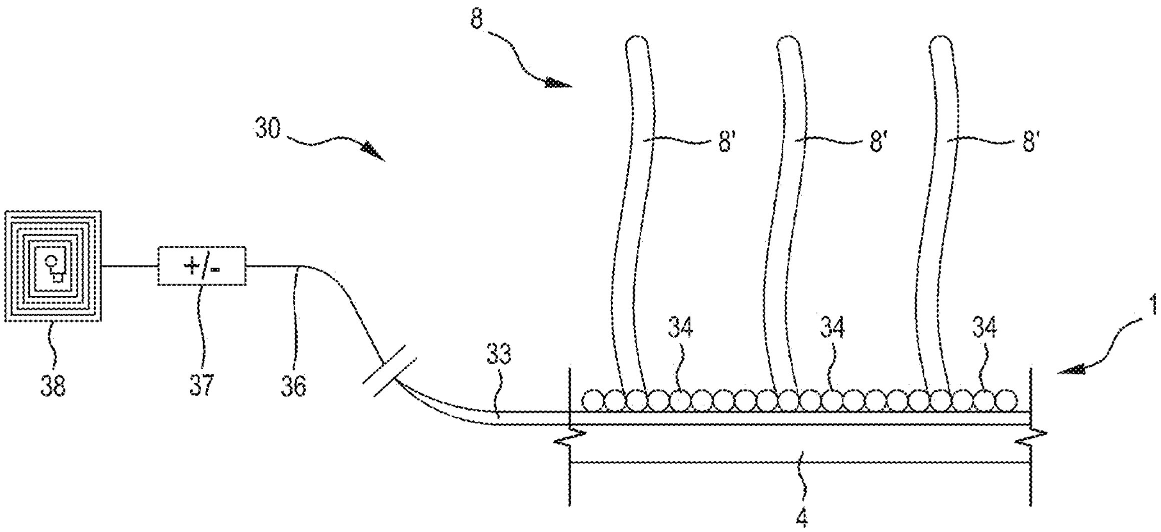
FIG. 27 is a schematic close-up side view of part of a collector element of a diagnostic device according to another preferred embodiment.

With reference to FIG. 27 of the drawings, another embodiment of a diagnostic device 30 is illustrated. In this example, the diagnostic device 30 again includes a sample collection device 1 for collecting a nasal sample having a frame 2, a central portion 3 and rib members 4 carrying collector pads 8 of flocked fibres 8', as per the embodiment seen in FIG. 26*a*, with individual fibre flocking 8' of the collector pad 8 again visible. Further, a reagent 34 is again provided or carried on a substrate 33 of the test or assay 31 within or adjacent to the collector pad 8. The substrate 33 in this embodiment, however, forms a polarisation sensor. The substrate 33 is therefore electrically conducting and in electrical connection via wiring 36 with a switch 37, e.g., a polarisation switch, and communication means 38, such as an NFC tag. The sample collected by the pads 8 makes contact with the reagent 34 provided or carried on the substrate 33 of the test or assay 31 within or adjacent to each collector pad 8. Any resultant interaction of the reagent 34 with the target substance or compound in the sample is designed to produce an electrical potential or polarisation which is transmitted or detected by the switch 37. The switch 37 then enables the NFC tag 38 to be activated by and/or to communicate with a mobile device (not shown) such as a mobile smart phone operating a suitable software application. In this way, the software application on the smart phone may display the test result to the individual. It may also record that test result and/or communicate the test result to a government health authority and/or to a medical care team.

Although specific embodiments of the disclosure are illustrated and described herein, it will be appreciated by persons of ordinary skill in the art that a variety of alternative and/or equivalent implementations exist. It should be appreciated that each exemplary embodiment is an example only and is not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

It will also be appreciated that the terms "comprise", "comprising", "include", "including", "contain", "containing", "have", "having", and any variations thereof, used in this document are intended to be understood in an inclusive (i.e. non-exclusive) sense, such that the process, method, device, apparatus, or system described herein is not limited to those features, integers, parts, elements, or steps recited but may include other features, integers, parts, elements, or steps not expressly listed and/or inherent to such process, method, device, apparatus, or system. Furthermore, the terms "a" and "an" used herein are intended to be understood as meaning one or more unless explicitly stated otherwise. Moreover, the terms "first", "second", "third", etc. are used merely as labels, and are not intended to impose numerical requirements on or to establish a certain ranking of importance of their objects. In addition, reference to positional terms, such as "lower" and "upper", used in the above description are to be taken in context of the embodiments depicted in the figures, and are not to be taken as limiting the disclosure to the literal interpretation of the term but rather as would be understood by the skilled addressee in the appropriate context.

The invention claimed is:

1. A sample collection device for collection of a nasal sample from an individual, the sample collection device comprising:

a substrate configured to be received and retained within a nostril of the individual; and a collector element provided on or carried by the substrate for receiving and collecting the nasal sample, wherein the collector element is provided on or carried by the substrate such that, when the substrate is retained or accommodated within the nostril, the collector element contacts or engages with tissue of the nostril to receive and collect the sample;

wherein the substrate forms a frame of the device for supporting the collector element provided and/or carried thereon; wherein the frame comprises at least one frame member configured to be received and retained or accommodated within the nostril of the individual, and wherein the collector element is provided on and/or carried by the frame member;

wherein the sample collection device is wearable, such that, in use, the device is configured to be wearable or be worn by the individual within the nostril of the individual such that the collector element is received and retained or accommodated within the nostril of the individual for a sample collection time;

wherein the at least one frame member on which the collector element is provided or carried is configured to be received and retained or accommodated within a lower nasal cavity of the nostril for receiving and collecting the nasal sample;

wherein the least one frame member comprises a curved or looped configuration, and wherein the least one frame member is elongated and formed to complement a surface profile or curvature of the nasal cavity, and wherein the collector element is provided and/or carried on a surface or region of the frame member that faces a tissue of the nasal cavity; and wherein the at least one frame member on which the collector element is provided or carried is broader or wider in a region configured to be located deeper within the nasal cavity.

2. The sample collection device according to claim 1, wherein:

the at least one frame member on which the collector element is provided is elongate and extends as a rib which follows a profile or curvature of an inner surface of the nostril.

3. The sample collection device according to claim 1, wherein the at least one frame member is divided, splayed or open in the broader or wider region to provide a greater surface area for supporting the collector, thereby to increase a potential sample load.

4. The sample collection device according to claim 1, wherein the sample collection time is an extended or predetermined sample collection time.

5. A sample collection device for collection of a nasal sample from an individual, the sample collection device comprising:

a frame having at least one frame member configured to be received and retained or accommodated within a nostril of the individual; and a collector element provided on and/or carried by the at least one frame member for receiving and collecting the nasal sample;

wherein the collector element is provided on and/or carried by the frame member such that, when the frame member is retained or accommodated within a nostril, the collector element contacts and/or engages with an inner surface or tissue of the nasal cavity to receive and collect the sample;

wherein the sample collection device is wearable, such that, in use, the device is configured to be wearable or be worn by the individual within the nostril of the individual such that the collector element is received and retained or accommodated within the nostril of the individual for a sample collection time;

wherein the at least one frame member on which the collector element is provided or carried thereon is configured to be received and retained or accommodated within a lower nasal cavity of the nostril for receiving and collecting the nasal sample;

wherein the least one frame member comprises a curved or looped configuration, and wherein the least one frame member is elongated and formed to complement a surface profile or curvature of the nasal cavity, and wherein the collector element is provided and/or carried on a surface or region of the frame member that faces a tissue of the nasal cavity; and wherein the at least one frame member on which the collector element is provided or carried is broader or wider in a region configured to be located deeper within the nasal cavity.

6. A sample collection device according to claim 5, wherein the at least one elongated frame member is resiliently flexible and biased into contact with the nasal cavity so that the collector element bears against and/or engages with tissue of the nasal cavity when the at least one frame member is accommodated within a nostril.

7. A sample collection device according claim 5, wherein:

(a) the at least one frame member comprises a pair of frame members, each of which is configured to be accommodated within a respective one of the nostrils of the individual, wherein the device comprises a respective collector element provided on and/or carried by each of the frame members such that each collector element bears against or engages with the tissue of the respective nostril to receive and collect the sample; and/or (b) each one of the pair of frame members has a curved or looped configuration.

8. A sample collection device according to claim 5, wherein the collector element is adapted to be separated or removed from the frame to harvest the sample collected thereon for testing.

9. A sample collection device according to claim 5, wherein the collector element is configured in a form of a sleeve of collector material configured to extend over an outer periphery of the respective frame member on which the collector element is provided and/or carried, wherein the sleeve of collector material is removable from the frame member to harvest the sample collected thereon for testing.

10. A sample collection device according to claim 5, wherein the collector element is configured in a form of a pad which is fixed at one or more connection points to the respective frame member on which the collector element is provided or carried thereon, wherein the one or more connection points are releasable or frangible to permit separation or removal of the collector element from the frame upon application of a force.

11. A sample collection device according to claim 5, wherein the at least one frame member includes a separation point at which the at least one frame member is adapted to be physically separated or removed from the frame to harvest the sample collected on the collector element for testing.

12. A sample collection device according to claim 11, wherein the separation point comprises a point of weakness or a fracture point at which the at least one frame member is configured to be broken away from the frame upon application of a force.

13. A sample collection device according to claim 11, wherein the separation point comprises a region of reduced thickness in the frame or a necked or notched region of the frame member.

14. The sample collection device according to claim 5, wherein:

the at least one frame member on which the collector element is provided is elongate and extends as a rib which follows a profile or curvature of an inner surface of the nostril.

15. The sample collection device according to claim 5, wherein the at least one frame member is divided, splayed or open in the broader or wider region to provide a greater surface area for supporting the collector, thereby to increase a potential sample load.

16. The sample collection device according to claim 5, wherein the nasal sample is in a liquid or semi-solid form.

17. The sample collection device according to claim 5, wherein the sample collection time is an extended or predetermined sample collection time.

18. A sample collection device according to claim 5, wherein:

(a) the frame includes a handle portion for manual handling of the sample collection device by the individual, wherein the at least one frame member extends from the handle portion of the frame, and the handle portion is releasably connected to each frame member; and/or (b) wherein the collector element comprises a collector material for receiving and collecting the nasal sample, the collector material being comprised of fibers.

19. A sample collection device according to claim 5, wherein the frame includes a sample collection accelerator to promote excretion of nasal mucus by an individual using the sample collection device.

20. A sample collection device according to claim 5, wherein the frame of the device comprises a framework structure comprising an array, web, or mesh of strand-like elements or filaments, wherein the strand-like elements or filaments comprise a polymer plastic material and are fused or bonded together.

21. A sample collection device according to claim 5, wherein the collector element provided on or carried by the frame of the device for receiving and collecting the sample comprises an open framework and/or an array, web, or mesh of strand-like elements or filaments, that comprises an outer layer or covering on the frame of the device.

22. A sample collection kit, comprising: a sample collection device according to claim 5, and a sample container for receiving and storing the collector element and the sample collected thereon for transport and testing.

23. A sample collection system, comprising a sample collection device for collecting a nasal sample according to claim 5 and a software application for supporting use of the sample collection device by an individual.

24. A diagnostic kit, comprising a sample collection device according to claim 5 for collecting a nasal sample, and a sample test or assay provided in association with the sample collection device for testing a collected sample for presence of a target substance or compound in the sample.

25. A diagnostic device, comprising a sample collection device according to claim 5 for collecting a nasal sample, and a sample test or assay on the frame of the sample collection device for testing a sample collected therewith for presence of a target substance or compound.

26. A frame of a sample collection device for collecting a nasal sample from an individual, wherein the sample collection device is a sample collection device of claim 5, and wherein the frame comprising: at least one frame member configured to be received and retained or accommodated within a nostril of the individual, wherein the at least one frame member is configured or adapted to carry or support a collector element for receiving and collecting the nasal sample, such that, when the frame member is retained or accommodated within a nostril, the collector element is positioned to contact or engage with an inner surface or tissue of the nasal cavity to receive and collect the sample.

27. A method of collecting a nasal sample from an individual, the method comprising steps of:

providing the sample collection device according to claim 5 comprising a frame, at least part of which is configured to be received and retained within a nostril of the individual, and a collector element provided on and/or carried by said part of the frame for receiving and collecting the nasal sample;

introducing the collector element provided on and/or carried by the said part of the frame into a nostril of the individual, whereby the collector element is received and retained within the nostril, such that the collector element contacts or engages with an inner surface or tissue of the nostril to receive and collect the nasal sample;

allowing the collector element provided on and/or carried by said part of the frame to remain or reside within the nostril for a period of time for nasal sample collection; and removing said part of the frame and the collector provided element and/or carried thereon from the nostril to harvest the nasal sample.

28. The method of collecting a nasal sample from an individual according to claim 27, wherein the period of time is a predetermined period of time.

* * * * *